US010556004B2

(12) United States Patent
Koshi et al.

(10) Patent No.: US 10,556,004 B2
(45) Date of Patent: Feb. 11, 2020

(54) IMMUNOPOTENTIATOR

(71) Applicant: TORAY INDUSTRIES, INC., Tokyo (JP)

(72) Inventors: Yoichiro Koshi, Kamakura (JP); Joonsik Park, Kamakura (JP); Jiao Lu, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 137 days.

(21) Appl. No.: 15/028,266

(22) PCT Filed: Oct. 9, 2014

(86) PCT No.: PCT/JP2014/077038
§ 371 (c)(1),
(2) Date: Apr. 8, 2016

(87) PCT Pub. No.: WO2015/053354
PCT Pub. Date: Apr. 16, 2015

(65) Prior Publication Data
US 2016/0256543 A1 Sep. 8, 2016

(30) Foreign Application Priority Data

Oct. 9, 2013 (JP) ................................. 2013-212103

(51) Int. Cl.
*A61K 39/39* (2006.01)
*A61K 39/00* (2006.01)
*A61K 9/16* (2006.01)

(52) U.S. Cl.
CPC ................ *A61K 39/39* (2013.01); *A61K 9/16* (2013.01); *A61K 39/0011* (2013.01); *A61K 2039/55583* (2013.01)

(58) Field of Classification Search
CPC .............. A61K 31/7032; A61K 31/716; A61K 31/719; A61K 47/48; A61K 47/48092; A61K 47/48169; A61K 47/4823; A61K 47/4833; A61K 47/593; A61K 39/39
See application file for complete search history.

(56) References Cited

U.S. PATENT DOCUMENTS

| | | | | |
|---|---|---|---|---|
| 3,871,892 A * | 3/1975 | Hijiya | ................. | C08B 37/0018 106/135.1 |
| 5,032,401 A * | 7/1991 | Jamas | ................. | A61K 9/1652 424/278.1 |
| 5,804,199 A | 9/1998 | Aasjord et al. | | |
| 8,431,161 B2 * | 4/2013 | Kakizawa | ............ | A61K 9/1647 424/499 |
| 2004/0057958 A1 | 3/2004 | Waggoner, Jr. et al. | | |
| 2010/0266626 A1 | 10/2010 | Berti et al. | | |
| 2011/0003007 A1 * | 1/2011 | Kakizawa | ............ | A61K 9/1647 424/499 |
| 2011/0045015 A1 | 2/2011 | Berti et al. | | |
| 2011/0135679 A1 | 6/2011 | Malyala et al. | | |
| 2011/0300223 A1 | 12/2011 | Nishio et al. | | |
| 2013/0156859 A1 | 6/2013 | Koshi et al. | | |
| 2013/0315960 A1 | 11/2013 | Berti et al. | | |

FOREIGN PATENT DOCUMENTS

| | | |
|---|---|---|
| EP | 1602377 A1 | 12/2005 |
| EP | 2609931 A1 | 7/2013 |
| JP | 7-53404 A | 2/1995 |
| JP | 10-194977 A | 7/1998 |
| JP | 2007-269791 A | 10/2007 |
| JP | 2009-256324 A | 11/2009 |
| JP | 2011-504487 A | 2/2011 |
| JP | 2011-504535 A | 2/2011 |
| JP | 2011-506334 A | 3/2011 |
| JP | 2013-67709 A | 4/2013 |

OTHER PUBLICATIONS

Tada, R., et al., Glycoconj. J.. 25: 851-861, 2008.*
Jeong, Y.-I., et al., International Journal of Pharmaceutics, 322: 154-160, 2006.*
Lee, S.G., et al., Surface & Coatings Technology 201: 5128-5131, 2007.*
Misaki, A., et al., Carbohydrate Research, 129: 209-227, 1984; Abstract Only.*
Lehtovaara, B.C., et al., Journal of Agricultural and Food Chemistry, 59: 6813-6828, 2011.*
Kimura, Y. et al., Anticancer Research, 26: 4131-4142, 2006.*
Chen et al., "Medicinal importance of fungal • -(1-->3), (1-->6)-glucans", Mycological Research 111 (2007), pp. 635-652, www.elsevier.com/locate/mycres.
International Search Report, issued in PCT/JP2014/077038, dated Jan. 13, 2015.
Ouchi et al., "Modification of polylactide upon physical properties by solution-cast blends from polylactide and polylactide-grafted dextran", Polymer 44; 2003; pp. 3927-3933. www.elsevier.com/locate/polymer.
Tetsuya Suga et al., "Mitherapist Cho Biryushi • -glucan", Associate journal of Japanese Society for Medical Use of Functional Foods, 2005, vol. 2, No. 4, pp. 219-227.
Tetsuya Suga, "Bisaika Gijutsu ni yoru Kinosei Shokuhin no Kenkyu Kaihatsu", Food Processing and Ingredients, 2006, vol. 41, No. 2, pp. 4-6.
Written Opinion of the International Searching Authority, issued in PCT/JP2014/077038 (PCT/ISA/237), dated Jan. 13, 2015.
Bohn et al., "(1→3)-β-$_D$-Glucans as biological response modifiers: a review of structure-functional activity relationships," Carbohydrate Polymers, vol. 28, Iss. 1, Jan. 1995, pp. 3-14.
Extended European Search Report issued in European Application No. 14852637.9, dated May 11, 2017.
Huang et al., "Distinct Patterns of Dendritic Cell Cytokine Release Stimulated by Fungal β-Glucans and Toll-Like Receptor Agonists," Infection and Immunity, vol. 77, No. 5, May 2009 (Published ahead of print Mar. 9, 2009), XP007915686, pp. 1774-1781.
Australian Office Action issued in Application No. 2014332835 dated Jan. 22, 2019.
Russian Office Action, dated Jan. 28, 2019, for Russian Application No. 2016116786, along with an English translation.

* cited by examiner

*Primary Examiner* — Karen A. Canella
(74) *Attorney, Agent, or Firm* — Birch, Stewart, Kolasch & Birch, LLP

(57) ABSTRACT

There is provided an immunopotentiator comprising, as an active ingredient, a modified β-glucan which β-glucan and poly(hydroxy acid) are covalently bonded. The immunopotentiator can potently enhance the immunopotentiating effect of β-glucan.

10 Claims, 11 Drawing Sheets a. Curdlan hydrolysate (4)
b. Curdlan hydrolysate (5)
c. Curdlan hydrolysate (6)

Modified curdlan (9)

IMMUNOPOTENTIATOR

CROSS-REFERENCE TO RELATED APPLICATIONS

This application is based upon and claims the benefit of priority from Japanese Patent Application No. 2013-212103, filed on Oct. 9, 2013; the entire contents of which are incorporated herein by reference.

FIELD OF THE INVENTION

The present invention relates to an immunopotentiator comprising, as an active ingredient, a modified β-glucan which β-glucan and poly(hydroxy acid) are covalently bonded.

BACKGROUND ART

Polysaccharides are known to have various effects on the organism. Of these, β-glucans are known to bind to receptors (e.g., Dectin-1) and the like existing in immune cells in the organism to activate immunoreaction (see Non Patent Document 1). Although immunopotentiators utilizing the immunopotentiating effect of β-glucans have been researched and developed (see Patent Document 1), the immunopotentiating effect of β-glucans cannot be said to be potent, and concomitant use with other immunopotentiators to obtain sufficient effects has been investigated (see Patent Document 2).

Meanwhile, polysaccharides are also known as the materials of biocompatibility, and they are used as the bases of hydrogel or sustained release materials by utilizing the biocompatibility of polysaccharides. Modification of biodegradable polymers to polysaccharides can transform the physical properties while maintaining the biocompatibility (see Patent Document 3 and Non Patent Document 2).

PRIOR ART REFERENCES

Patent Documents

[Patent Document 1]
Japanese Patent Application Laid-Open Publication No. 1998-194977
[Patent Document 2]
Japanese Patent Application Laid-Open Publication No. 2011-504487
[Patent Document 3]
Japanese Patent Application Laid-Open Publication No. 2013-67709

Non Patent Documents

[Non Patent Document 1]
Mycological Research, 2007; 111:635-652
[Non Patent Document 2]
Polymer 2003; 44: 3927-3933

SUMMARY OF THE INVENTION

Problems to be Solved by the Invention

An object of the present invention is to provide a potent immunopotentiator by enhancing the immunopotentiating effect of β-glucan.

Means for Solving the Problems

In order to overcome the above problem, the present inventor investigated a means to enhance the immunopotentiating effect of β-glucan, found that β-glucan modified with poly(hydroxy acid) has high in vivo immunopotentiating capacity, and completed the present invention.

In other words, the present invention has the following (1) to (12) constitutions.

(1) An immunopotentiator comprising, as an active ingredient, a modified β-glucan which β-glucan and poly(hydroxy acid) are covalently bonded.

(2) The immunopotentiator according to (1), wherein β-glucan is a polymer of glucose linked by at least one β-1,3 bond and/or at least one β-1,6 bond.

(3) The immunopotentiator according to (1) or (2), wherein modified β-glucan is a graft type polymer composed of the main chain of β-glucan and the side chain of poly(hydroxy acid).

(4) The immunopotentiator according to any one of (1) to (3), wherein the proportion of β-glucan segments is 1% to 50% (w/w).

(5) The immunopotentiator according to any one of (1) to (4), wherein β-glucan is curdlan, laminaran, pachyman, lichenan, sizofiran, lentinan, scieroglucan, *Aureobasidium pullulans* glucan, or pachymaran.

(6) The immunopotentiator according to any one of (1) to (5), wherein the number average molecular weight of β-glucan is 500 to 100,000.

(7) The immunopotentiator according to any one of (1) to (6), wherein poly(hydroxy acid) is a poly(lactic-co-glycolic acid), polylactic acid, or polyglycolic acid.

(8) The immunopotentiator according to any one of (1) to (7), which comprises a particle of a modified β-glucan as an active ingredient.

(9) A medicine comprising the immunopotentiator according to any one of (1) to (8) as an active ingredient.

(10) A vaccine comprising the immunopotentiator according to any one of (1) to (8) and an antigen as active ingredients.

(11) A vaccine for the treatment and/or prevention of cancer, comprising the immunopotentiator according to any one of (1) to (8) and a cancer antigen as active ingredients.

(12) A method for the immunopotentiation, which comprises administering in vivo the immunopotentiator according to any one of (1) to (8) or the medicine according to (9).

Effects of the Invention

The present invention provides an immunopotentiator that activates immunity more potently than conventional one.

MODE FOR CARRYING OUT THE INVENTION

Figure 1:
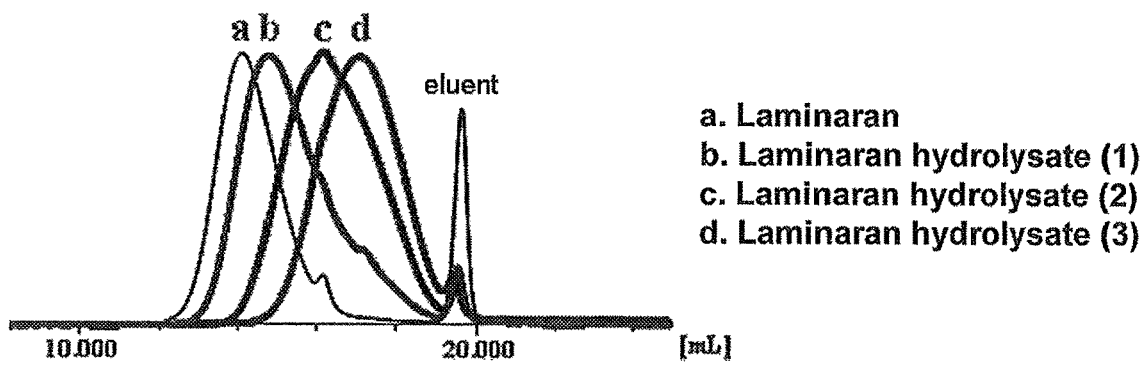
FIG. 1 shows the results of GPC measurement of laminaran and laminaran hydrolysates (1) to (3).

The present invention relates to an immunopotentiator comprising, as an active ingredient, a modified β-glucan which β-glucan and poly(hydroxy acid) are covalently bonded.

Glucan is a polysaccharide containing glucose, and β-glucan is a glucan containing at least one β-bond between glucose subunits. In other words, β-glucan used in the present invention is a glucan containing a β-bond, and may be a glucan containing only a β-bond. β-Glucan used in the present invention may be branched or linear.

Preferable β-glucan used in the present invention includes β-glucan that contains at least one β-1,3 bond and/or at least one β-1,6 bond, or β-glucan that contains at least one β-1,2 bond and/or β-1,4 bond, more preferably β-glucan that contains at least one β-1,3 bond and/or at least one β-1,6 bond, and still more preferably β-glucan that contains at least one β-1,3 bond. Examples of β-glucan that contains at least one β-1,3 bond include curdlan, pachyman, laminaran, lichenan, sizofiran, lentinan, scleroglucan, *Aureobasidium pullulans* glucan (preferably *Aureobasidium pullulans*-derived β-1,3 glucan or β-1,6 glucan), or pachymaran, preferably curdlan, pachyman, laminaran, sizofiran, scleroglucan, *Aureobasidium pullulans* glucan, or pachymaran.

Linear β-glucan that contains at least one (β-1,3 bond includes β-glucan that is mainly composed of a β-1,3 bond (for example, curdlan or pachyman) or β-glucan that is composed of a β-1,3 bond and a β-bond other than β-1,3 bond (for example, laminaran or lichenan).

Branched β-glucan that contains at least one β-1,3 bond includes β-glucan that is composed of a β-1,3 bond and a β-1,6 bond (for example, sizofiran, lentinan, scleroglucan, or *Aureobasidium pullulans* glucan).

β-Glucan used in the present invention may be derivatized. Examples of derivatization include addition reaction of a carboxymethyl group or oxidative cleavage reaction. Examples of derivatized β-glucan include carboxymethyl curdlan in which a carboxymethyl group is added to curdlan or pachymaran in which pachyman is cleaved.

There is no particular limitation on the number average molecular weight of β-glucan, and it is preferably 500 to 100,000, more preferably 1,000 to 50,000, and still more preferably 1,900 to 25,000. The number average molecular weight is the average molecular weight calculated by not considering the weighting of molecular size, and the number average molecular weight of β-glucan can be calculated by gel permeation chromatography (GPC).

There is no particular limitation on poly(hydroxy acid), and it is preferably a biocompatibility polymer that has no marked adverse effects at the time of in vivo administration in terms of the component of an immunopotentiator. The term biocompatibility here means that in which LD50 when the polymer is orally administered to rats is 2,000 mg/kg or more. Poly(hydroxy acid) may be a copolymer of plural types of hydroxy acids, and is preferably a polymer of two or less types of hydroxy acids.

Preferable specific examples of poly(hydroxy acid) include polyglycolic acid, polylactic acid, poly(2-hydroxybutyric acid), poly(2-hydroxyvaleric acid), poly(2-hydroxycaproic acid), poly(2-hydroxycapric acid), poly(malic acid), or a derivative and a copolymer of these high molecular compounds, and poly(lactic-co-glycolic acid), polylactic acid, or polyglycolic acid is more preferable, and poly (lactic-co-glycolic acid) is still more preferable. There is no particular limitation on the composition ratio of poly(lactic-co-glycolic acid) (lactic acid/glycolic acid) (mol/mol) when poly(hydroxy acid) is poly(lactic-co-glycolic acid) as long as the object of the present invention is achieved, and it is preferably 100/0 to 30/70, and more preferably 60/40 to 40/60.

There is no particular limitation on the number average molecular weight of poly(hydroxy acid), and it is preferably 500 to 1,000,000, more preferably 10,000 to 100,000, and still more preferably 14,700 to 68,300. The number average molecular weight of poly(hydroxy acid) can be calculated from the difference between the number average molecular weight of modified β-glucan and the number average molecular weight of β-glucan.

There is not particular limitation on the structure of modified β-glucan, and examples of it include a linear block type polymer in which β-glucan is linked with poly(hydroxy acid), a branched polymer having plural branched chains of β-glucans or poly(hydroxy acids), a graft type polymer composed of the main chain of β-glucan and the side chain of poly(hydroxy acid), or a graft type polymer composed of the main chain of poly(hydroxy acid) and the side chain of β-glucan, preferably a graft type polymer composed of the main chain of β-glucan and the side chain of poly(hydroxy acid).

Since modified β-glucan sustains the immunopotentiating effect for a long time, it is preferably water-insoluble as a whole so that it is not immediately excreted in vivo. The term water-insolubility here means that the solubility in water is 1 g (modified β-glucan)/100 ml (water) or less.

There is no particular limitation on the number average molecular weight of modified β-glucan, and it is preferably 1,000 to 1,000,000, more preferably 10,000 to 100,000, and still more preferably 13,800 to 84,000. The number average molecular weight of modified β-glucan can be calculated by gel permeation chromatography (GPC).

There is no particular limitation on the proportion of β-glucan segments in modified β-glucan (β-glucan segments/modified β-glucan), and it is preferably 1% to 50% (w/w), more preferably 5% to 45% (w/w), and still more preferably 8.3% to 42.5% (w/w). The proportion of β-glucan segments in modified β-glucan can be calculated by using the proportion of the number average molecular weight of β-glucan to the number average molecular weight of modified β-glucan.

For a graft type polymer composed of the main chain of β-glucan and the side chain of poly(hydroxy acid), there is no particular limitation on the number average molecular weight of each graft chain, and it is preferably 1,000 to 10,000, and more preferably 1,300 to 6,400. The number average molecular weight of each graft chain can be calculated from the ratio of the peak integral value of a terminal residue to the peak integral value of the sites other than the terminal residue by nuclear magnetic resonance (NMR) measurement.

For a graft type polymer composed of the main chain of β-glucan and the side chain of poly(hydroxy acid), there is no particular limitation on the number of graft chains, and it is preferably 3 to 15. The number of graft chains can be calculated by dividing the value obtained by subtracting the number average molecular weight of β-glucan from the number average molecular weight of modified β-glucan by the number average molecular weight of each graft chain.

Modified β-glucan may be produced by known methods, specifically, examples include a method for producing by adding poly(hydroxy acid) to β-glucan to perform condensation reaction or a method for producing by adding hydroxy acid-activated monomer to β-glucan to perform polymerization reaction.

Particularly, when modified β-glucan is a graft type polymer composed of the main chain of β-glucan and the side chain of poly(hydroxy acid), it can be produced by the following (1), (2), or (3):

(1) A method for producing a graft type polymer by, in the presence of tin catalysts, adding hydroxy acid-activated monomer to β-glucan to perform polymerization reaction and by introducing poly(hydroxy acid) [Macromolecules 1998; 31: p. 1032-1039]

(2) A method for producing a graft type polymer by activating partially unprotected hydroxy groups of β-glucan in which the majority of hydroxy groups are protected by substituents with bases, then by adding hydroxy acid-activated monomer to introduce graft chains composed of poly(hydroxy acid), and finally by removing the protecting groups [Polymer 2003; 44: 3927-3933]

(3) A method for producing a graft type polymer by performing condensation reaction of a copolymer of poly(hydroxy acid) with β-glucan using dehydrating agents and/or functional group-activating agents [Macromolecules 2000; 33:3680-3685].

The form of modified β-glucan used as an immunopotentiator includes fiber, film, particle, and the like, and when an immunopotentiator is administered in vivo, particle is preferable in terms of ease of administration.

There is no particular limitation on a method for producing a modified β-glucan particle, and it includes a solvent evaporation method, a spray drying method, or a crushing method, and a modified β-glucan particle is preferably produced by the solvent evaporation method.

A method for producing a particle by the solvent evaporation method includes an O/W emulsion method, a W/O/W emulsion method, or an S/O/W emulsion method.

As an example of the production of a particle by the O/W emulsion method, the particle can be produced in a process in which a water-immiscible organic solvent in which a modified β-glucan is dissolved is mixed with a surface modifier aqueous solution to prepare an O/W emulsion solution, and a process in which the water-immiscible organic solvent is removed from the O/W emulsion solution to obtain the particle.

As an example of the production of a particle by the W/O/W emulsion method, the particle can be produced in a process in which an aqueous solvent is mixed with a water-immiscible organic solvent in which a modified β-glucan is dissolved to prepare a W/O emulsion solution, a process in which the W/O emulsion solution is mixed with a surface modifier aqueous solution to prepare a W/O/W emulsion solution, and a process in which the water-immiscible organic solvent is removed from the W/O/W emulsion solution to obtain the particle.

As an example of the production of a particle by the S/O/W emulsion method, the particle can be produced in a process in which an aqueous solvent is mixed with a water-immiscible organic solvent in which a modified β-glucan is dissolved to prepare a W/O emulsion solution, a process in which the solvent is removed from the W/O emulsion solution to obtain solid contents, a process in which the solid contents are dispersed in the water-immiscible organic solvent to obtain an S/O suspension solution, a process in which the S/O suspension solution is mixed with a surface modifier aqueous solution to prepare an S/O/W emulsion solution, and a process in which the water-immiscible organic solvent is removed from the S/O/W emulsion solution to obtain the particle.

A surface modifier used for the preparation of a particle is preferably a water-soluble polymer or a surfactant. The term water-soluble polymer here means a high molecular compound whose solubility in water is 1 g (hydrophilic polymer)/100 ml (water) or more.

Examples of a water-soluble polymer as the surface modifier include polyethylene glycol, polyvinylpyrrolidone, polyvinyl alcohol, polyethylenimine, polyacrylic acid, polymethacrylic acid, poly-1,3-dioxolane, 2-methacryloyloxyethyl phosphorylcholine polymer, poly-1,3,6-trioxane, polyamino acid, peptide, protein, saccharides, or polysaccharides, and more preferably polyvinyl alcohol.

Examples of a surfactant as the surface modifier include nonionic surfactants, such as polyoxyethylene polyoxypropylene glycol, sucrose fatty acid ester, polyoxyethylene fatty acid ester, polyoxyethylene sorbitan mono-fatty acid ester, polyoxyethylene sorbitan di-fatty acid ester, polyoxyethylene glycerin mono-fatty acid ester, polyoxyethylene glycerin di-fatty acid ester, polyglycerin fatty acid ester, polyoxyethylene castor oil, or polyoxyethylene hardened castor oil; alkyl sulfates, such as sodium lauryl sulfate, ammonium lauryl sulfate, or sodium stearyl sulfate, or lecithin, and more preferably polyoxyethylene polyoxypropylene glycol.

In a water-immiscible organic solvent used for the preparation of a particle, preferably a modified β-glucan is soluble and β-glucan is slightly soluble or insoluble. The solubility in water of the water-immiscible organic solvent is preferably 30 g (water-immiscible organic solvent)/100 ml (water) or less. Examples of the water-immiscible organic solvent include ethyl acetate, isopropyl acetate, butyl acetate, dimethyl carbonate, diethyl carbonate, methylene chloride, or chloroform.

An aqueous solvent used for the preparation of a particle is water or an aqueous solution containing water-soluble components. Examples of the water-soluble components include inorganic salts, saccharides, organic salts, amino acid, peptide, protein, or nucleic acid.

On the surface of a modified β-glucan particle, a surface modifier used in the production process may be bound. The term bond here may be noncovalent bond or covalent bond. Noncovalent bond is preferably hydrophobic interaction, and may be electrostatic interaction, hydrogen bond, or van der Waals force, or may be bond of combination of them.

The mean particle size of the particle is preferably 0.01 to 10 μm, and more preferably 0.1 to 1 μm. The mean particle size here was calculated by measurement of light scattering intensity distribution and diffusion coefficient using a dynamic light scattering device (DLS: for example, Otsuka Electronics Co., Ltd., ELS-Z) and by analysis by the cumulant method.

An immunopotentiator is a drug that activates immune response in vivo, and an immunopotentiator of the present invention is characterized by having a modified β-glucan as an active ingredient. There is no limitation of the type of immune response activated by the immunopotentiator, and the type of immune response to be caused include Th1 immune response or Th2 immune response. It is known that either immune response predominantly occurs depending on the types of antigen, administration site, or an administration method, and an immunopotentiator of the present invention can cause both Th1 and Th2 immune responses.

An immunopotentiator of the present invention can be used as a medicine alone or in combination with other drugs. When an immunopotentiator of the present invention is used in combination with other drugs, they may be combined and formulated, or they may be formulated independently in order to be administered separately.

There is no particular limitation on drugs used in combination with an immunopotentiator of the present invention, and an antigen is preferably used. The term antigen here is a substance that induces immunity in vivo and utilized as a vaccine for the treatment and/or prevention of diseases. Concomitant use of an immunopotentiator of the present invention with an antigen can enhance the immune response induced by the antigen.

Examples of an antigen include peptide, protein, glycoprotein, glycolipid, lipid, carbohydrate, nucleic acid, or polysaccharides, and virus, bacterial body, allergy-inducing substance, tissue, or cell containing them. Specifically, they include pollen-derived antigen, hepatitis A virus-derived antigen, hepatitis B virus-derived antigen, hepatitis C virus-derived antigen, hepatitis D virus-derived antigen, hepatitis E virus-derived antigen, hepatitis F virus-derived antigen, HIV virus-derived antigen, influenza virus-derived antigen, herpes virus (HSV-1 or HSV-2)-derived antigen, *Bacillus anthracis*-derived antigen, *Chlamydia*-derived antigen, *Streptococcus pneumoniae*-derived antigen, Japanese encephalitis virus-derived antigen, measles virus-derived antigen, rubella virus-derived antigen, *Clostridium tetani*-derived antigen, varicella virus-derived antigen, SARS virus-derived antigen, EB virus-derived antigen, papillomavirus-derived antigen, *Helicobacter pylori*-derived antigen, rabies virus-derived antigen, West Nile virus-derived antigen, hantavirus-derived antigen, *Streptococcus*-derived antigen, *Staphylococcus*-derived antigen, *Bordetella pertussis*-derived antigen, *Mycobacterium tuberculosis*-derived antigen, *Plasmodium*-derived antigen, poliovirus-derived antigen, various zoonosis-derived antigens, various food allergy-derived antigens, or self-antigen.

Other preferable examples of an antigen include cancer antigen. Cancer antigen is a substance derived from proteins that are specifically expressed on cancer cells, and exerts its effects on the treatment and/or prevention of cancer by the immune response after administered in vivo from the outside of the organism. Concomitant use of an immunopotentiator of the present invention with a cancer antigen can be used as a vaccine for the treatment and/or prevention of cancer.

When an immunopotentiator of the present invention is a modified β-glucan particle, an antigen is preferably encapsulated in the particle. A method for encapsulating an antigen in the modified β-glucan particle includes a method for producing the modified β-glucan particle by the W/O/W emulsion method or the S/O/W emulsion method using an antigen solution as an aqueous solvent.

When an antigen is encapsulated in a modified β-glucan particle, the encapsulation rate (antigen/modified β-glucan) is preferably 0.01% to 20% (w/w) and more preferably 0.1% to 10% (w/w). A method for determining the encapsulation rate includes a method for determining the encapsulation rate by gel electrophoresis or liquid chromatography after an antigen is extracted from a modified β-glucan particle using an organic solvent.

According to a preferable embodiment of the present invention, there is provided a method for immunopotentiation, which include administering an immunopotentiator or a medicine of the present invention to the organism (subject). There is no limitation on a method for activating (potentiating) the immunoreaction using an immunopotentiator or a medicine of the present invention, and the immunopotentiator or the medicine may be administered to the organism, or may be brought into contact with immunocytes extracted ex vivo. There is no particular limitation of a method for administration to the organism, and examples include subcutaneous administration, intracutaneous administration, intramuscular administration, transnasal administration, pulmonary administration, oral administration, transcutaneous administration, sublingual administration, intravaginal administration, intraperitoneal injection, or lymph node administration, and preferably intracutaneous administration or subcutaneous administration. The organism to be administered may be human or animals other than human, and is preferably human or livestock, or pig, cattle, bird, sheep, horse, donkey, goat, camel, dog, cat, ferret, rabbit, monkey, rat, mouse, or guinea pig raised as a pet or laboratory animal.

When an immunopotentiator of the present invention is used as a medicine (including vaccine), formulation may be performed by combining various pharmaceutically useful additives, and examples of additives include buffer, antioxidant, salt, polymer, or sugar.

The dose of modified β-glucan when an immunopotentiator of the present invention is used as a medicine is appropriately selected according to the administration method or the frequency of administration. For example, when an immunopotentiator of the present invention is subcutaneously administered to humans, 0.01 to 1,000 mg per administration as an amount of a modified β-glucan is administered.

The dose of other drugs such as antigen when an immunopotentiator of the present invention is used in combination with an antigen is preferably 0.001 to 100 mg.

According to a preferable embodiment of the present invention, there is provided an immunopotentiator including, as an active ingredient, a modified β-glucan which β-glucan and poly(hydroxy acid) are covalently bonded, wherein the β-glucan is curdlan, pachyman, laminaran, sizofiran, scleroglucan, *Aureobasidium pullulans* glucan, or pachymaran, and the poly(hydroxy acid) is poly(lactic-co-glycolic acid).

According to another preferable embodiment of the present invention, there is provided a vaccine including an immunopotentiator including, as an active ingredient, a modified β-glucan which β-glucan and poly(hydroxy acid) are covalently bonded and a cancer antigen as an active ingredient, wherein the β-glucan is curdlan, pachyman, laminaran, sizofiran, scleroglucan, *Aureobasidium pullulans* glucan, or pachymaran, and the poly(hydroxy acid) is poly(lactic-co-glycolic acid).

EXAMPLES

Examples are shown below, but the present invention is not limited by these Examples.

Example 1: Synthesis of Laminaran in which Poly(Lactic-Co-Glycolic Acid) is Modified (Modified Laminarans (1) to (8))

(1) Hydrolysis Reaction of Laminaran (Synthesis of Laminaran Hydrolysates (1) to (3)

After 10 g of laminaran (number average molecular weight 25,000, Tokyo Chemical Industry Co., Ltd.) was dissolved in 120 ml of dimethyl sulfoxide, 15 ml of 0.5 N hydrochloric acid solution was added, followed by stirring at 105° C. for 0.5 hour. The reaction solution was transferred to a dialysis membrane and dialyzed in water, and then freeze-dried to obtain a laminaran hydrolysate (1) (number average molecular weight 12,700) as a powder. Under the same conditions, a laminaran hydrolysate (2) (number average molecular weight 6,700) and a laminaran hydrolysate (3) (number average molecular weight 4,100) were synthesized by reaction for 1.5 hours and 2 hours, respectively.

The number average molecular weight of laminaran and laminaran hydrolysate was determined by GPC measurement (column, Tosoh Corporation TSK-gel G3000PW$_{XL}$-CP×2, acetic acid buffer solvent [10 mM, pH=5]; detector, RI; reference standard, pullulan) (FIG. 1: laminaran and laminaran hydrolysates (1) to (3)).

(2) Trimethylsilylation (TMS) Reaction of Laminaran (Synthesis of Trimethylsilylated Laminarans (1) to (4))

After 2.4 g of laminaran (number average molecular weight 25,000, Tokyo Chemical Industry Co., Ltd.) was added to 48 ml of formamide and the solution was heated to 80° C. To this solution, 48 ml of 1,1,1,3,3,3-hexamethyldisilazane was added dropwise over 20 minutes, followed by stirring at 80° C. for 2.5 hours. The reaction solution was transferred to a separatory funnel, and allowed to stand until it is separated to two layers. The upper layer was collected and concentrated under reduced pressure, and then 144 ml of methanol was added and the obtained solid was filtered and dried to obtain 3.14 g of a trimethylsilylated laminaran (1) as a white solid. In the same manner, a trimethylsilylated laminaran (2) was synthesized from the laminaran hydrolysate (1), a trimethylsilylated laminaran (3) was synthesized from the laminaran hydrolysate (2), and a trimethylsilylated laminaran (4) was synthesized from the laminaran hydrolysate (3).

Figure 3:
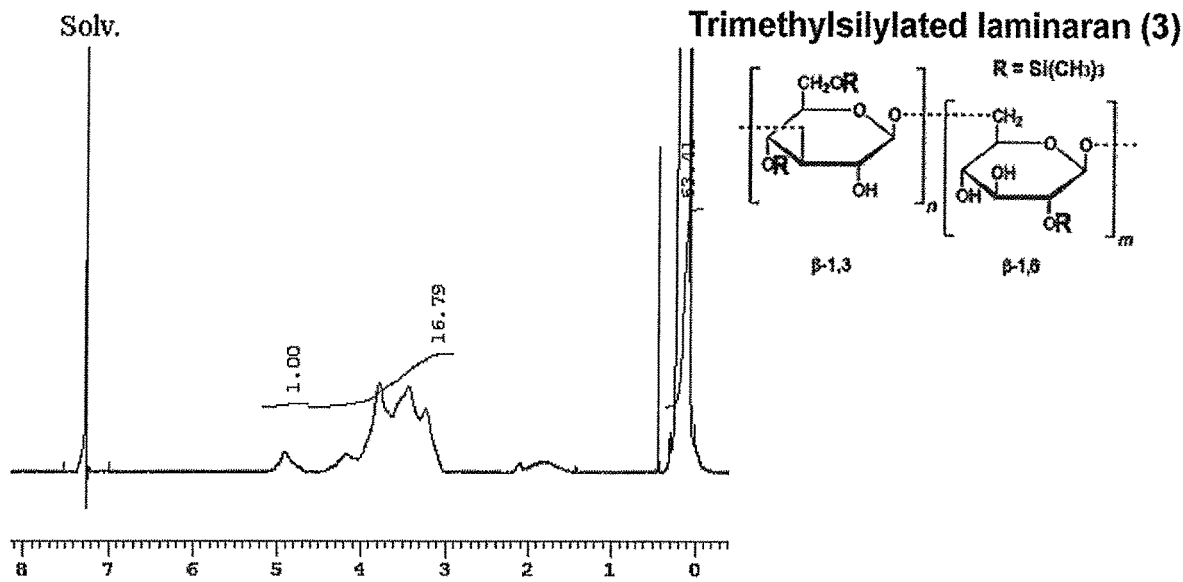
FIG. 3 shows the results of $^1$H-NMR measurement of trimethylsilylated laminaran (3).

The progress of trimethylsilylation reaction was confirmed by $^1$H-NMR measurement (FIG. 3: trimethylsilylated laminaran (3)).

(3) Modification Reaction of Poly(Lactic-Co-Glycolic Acid) to Laminaran (Synthesis of Modified Laminarans (1) to (8))

After 0.5 g of a trimethylsilylated laminaran (1) and 26 mg of tert-butoxypotassium (tBuOK) were dried with heating under reduced pressure for 2 hours, 10 ml of tetrahydrofuran was added, followed by stirring at room temperature for 1.5 hours to obtain an activated solution. A monomer (a mixture of (DL)-lactide and glycolide with a molar ratio of 1:1) of 35-fold mol of tBuOK used for the preparation of the activated solution was dissolved in tetrahydrofuran to obtain a monomer solution. The monomer solution was added dropwise to the activated solution, followed by stirring for 30 minutes, and then 0.5 ml of acetic acid was added to stop the reaction. The solution after completion of the reaction was concentrated under reduced pressure, and reprecipitated and purified with a chloroform (good solvent)-methanol (poor solvent) system and a chloroform (good solvent)-cyclohexane (poor solvent) system to obtain a white solid. The obtained white solid was dissolved in 5 ml of chloroform, and 0.5 ml of trifluoroacetic acid was added, followed by stirring at room temperature for 30 minutes. The reaction solution was concentrated under reduced pressure, and reprecipitated and purified with a chloroform (good solvent)-diethyl ether (poor solvent) system to obtain a modified laminaran (1) as a white solid.

In the same manner, a modified laminaran (2) was synthesized by reacting a trimethylsilylated laminaran (1) with a monomer of 50-fold mol of tBuOK, a modified laminaran (3) was synthesized by reacting a trimethylsilylated laminaran (2) with a monomer of 35-fold mol of tBuOK, a modified laminaran (4) was synthesized by reacting the trimethylsilylated laminaran (2) with a monomer of 50-fold mol of tBuOK, a modified laminaran (5) was synthesized by reacting the trimethylsilylated laminaran (3) with a monomer of 30-fold mol of tBuOK, a modified laminaran (6) was synthesized by reacting the trimethylsilylated laminaran (3) with a monomer of 35-fold mol of tBuOK, a modified laminaran (7) was synthesized by reacting the trimethylsilylated laminaran (3) with a monomer of 50-fold mol of tBuOK, and a modified laminaran (8) was synthesized by reacting the trimethylsilylated laminaran (4) with a monomer of 35-fold mol of tBuOK.

Figure 2:
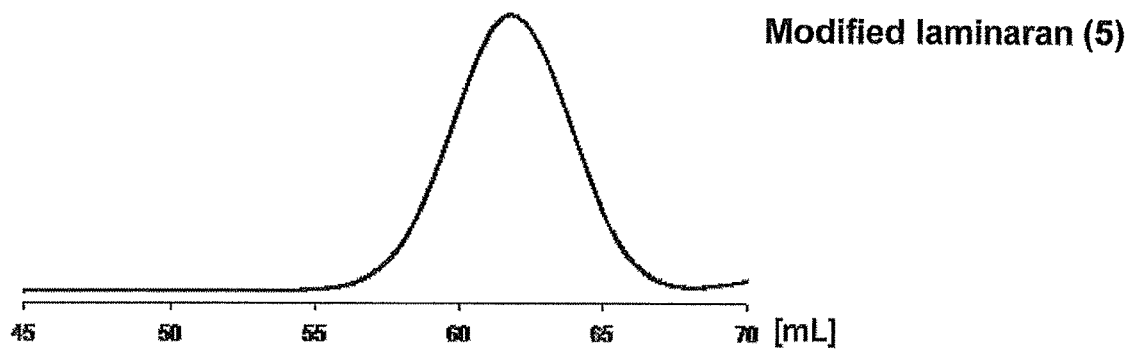
FIG. 2 shows the results of GPC measurement of a modified laminaran (5).
Figure 4:
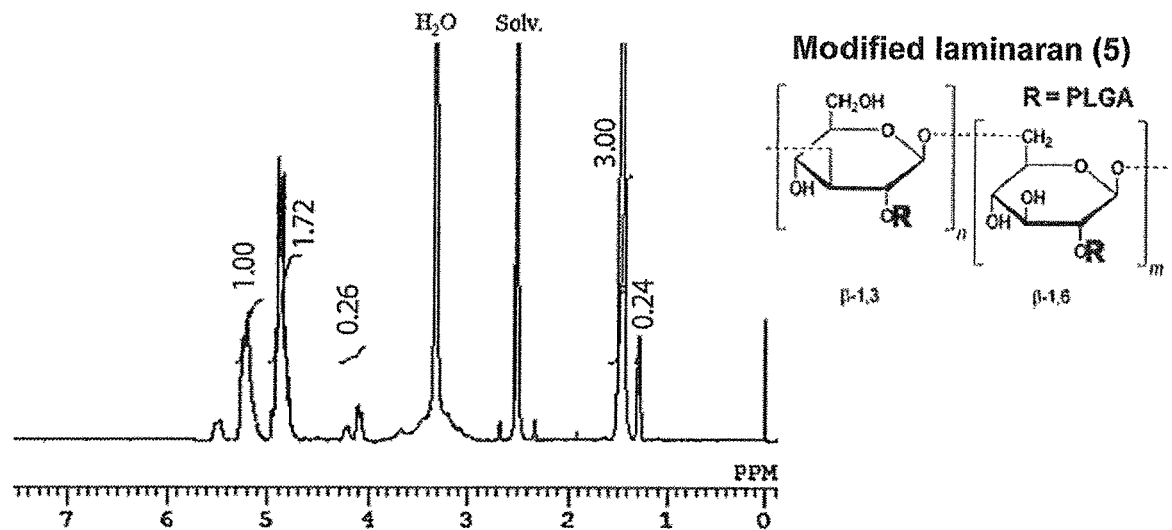
FIG. 4 shows the results of $^1$H-NMR measurement of a modified laminaran (5).

The results of assessment of modified laminarans (1) to (8) are shown in Table 1. The number average molecular weight of modified laminaran was determined by GPC measurement (column, Tosoh Corporation TSK-gel α-5000×2, DMF solvent; detector, RI; reference standard, pullulan) (FIG. 2: modified laminaran (5)). The proportion (w/w) of laminaran segments contained in the modified laminaran was determined from the number average molecular weight of laminaran used for the synthesis and the number average molecular weight of the modified laminaran. The number average molecular weight of each graft chain was determined by $^1$H-NMR measurement (FIG. 4: modified laminaran (5)). Mean number of graft chains was determined by dividing the value obtained by subtracting the number average molecular weight of laminaran from the number average molecular weight of the modified laminaran by the number average molecular weight of each graft chain.

TABLE 1

Results of analysis of modified laminarans (1) to (8)

| | Molecular weight of modified laminaran | Molecular weight of laminaran | Proportion of laminaran | Molecular weight of graft chain | Number of graft chains |
|---|---|---|---|---|---|
| Modified laminaran (1) | 67,000 | 25,000 | 37.3% | 3,700 | 11.4 |

TABLE 1-continued

Results of analysis of modified laminarans (1) to (8)

| | Molecular weight of modified laminaran | Molecular weight of laminaran | Proportion of laminaran | Molecular weight of graft chain | Number of graft chains |
|---|---|---|---|---|---|
| Modified laminaran (2) | 84,000 | | 29.8% | 4,400 | 13.4 |
| Modified laminaran (3) | 68,000 | 12,700 | 18.6% | 3,600 | 15.4 |
| Modified laminaran (4) | 81,000 | | 15.7% | 5,600 | 12.2 |
| Modified laminaran (5) | 29,000 | 6,700 | 23.1% | 1,600 | 13.4 |
| Modified laminaran (6) | 31,000 | | 21.6% | 1,900 | 12.8 |
| Modified laminaran (7) | 40,000 | | 16.8% | 3,300 | 10.1 |
| Modified laminaran (8) | 24,000 | 4,100 | 17.1% | 6,400 | 3.1 |

Example 2: Synthesis of Curdlan in which Poly(Lactic-Co-Glycolic Acid) is Modified (Modified Curdlans (9) to (14))

(1) Hydrolysis Reaction of Curdlan (Synthesis of Curdlan Hydrolysates (4) to (6))

After 12.8 g of curdlan (number average molecular weight, approximately 90,000, Wako Pure Chemical Industries, Ltd.) was dissolved in 384 ml of dimethyl sulfoxide and 19.2 ml of 1 N hydrochloric acid solution was added, followed by stirring at 110° C. for 0.75 hours. The reaction solution was transferred to a dialysis membrane and dialyzed in water, and then freeze-dried to obtain curdlan hydrolysate (4) (number average molecular weight 2,800) as a powder. Under the same conditions, a curdlan hydrolysate (5) (number average molecular weight 2,300) and a curdlan hydrolysate (6) (number average molecular weight 1,900) were synthesized by reaction for 0.8 hour and 0.85 hour, respectively.

Figure 5:
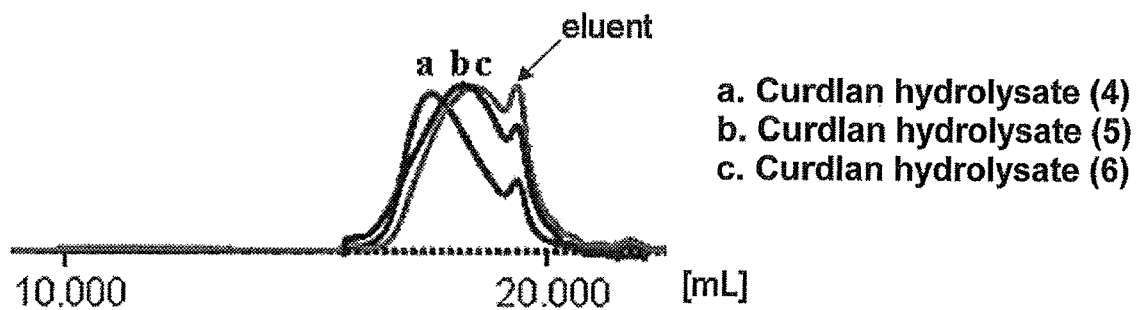
FIG. 5 shows the results of GPC measurement of curdlan hydrolysates (4) to (6).

The number average molecular weight of curdlan was determined by GPC measurement (column, Tosoh Corporation TSK-gel G3000PW$_{XL}$-CP×2, acetic acid buffer solvent [10 mM, pH=5]; detector, RI; reference standard, pullulan) (FIG. 5: curdlan hydrolysates (4) to (6)).

(2) Trimethylsilylation (TMS) Reaction of Curdlan (Synthesis of Trimethylsilylated Curdlans (5) to (7))

After 1 g of a curdlan hydrolysate (4) was added to 20 ml of formamide, the solution was heated to 80° C. To this solution, 20 ml of 1,1,1,3,3,3-hexamethyldisilazane was added dropwise over 20 minutes, followed by stirring at 80° C. for 2.5 hours. The reaction solution was transferred to a separatory funnel, and allowed to stand until it is separated to two layers. The upper layer was collected and concentrated under reduced pressure and 60 ml of methanol was added, and then the obtained solid was filtered and dried to obtain 1 g of a trimethylsilylated curdlan (5) as a white solid. In the same manner, a trimethylsilylated curdlan (6) was synthesized from the curdlan hydrolysate (5), and a trimethylsilylated curdlan (7) was synthesized from the curdlan hydrolysate (6).

Figure 7:
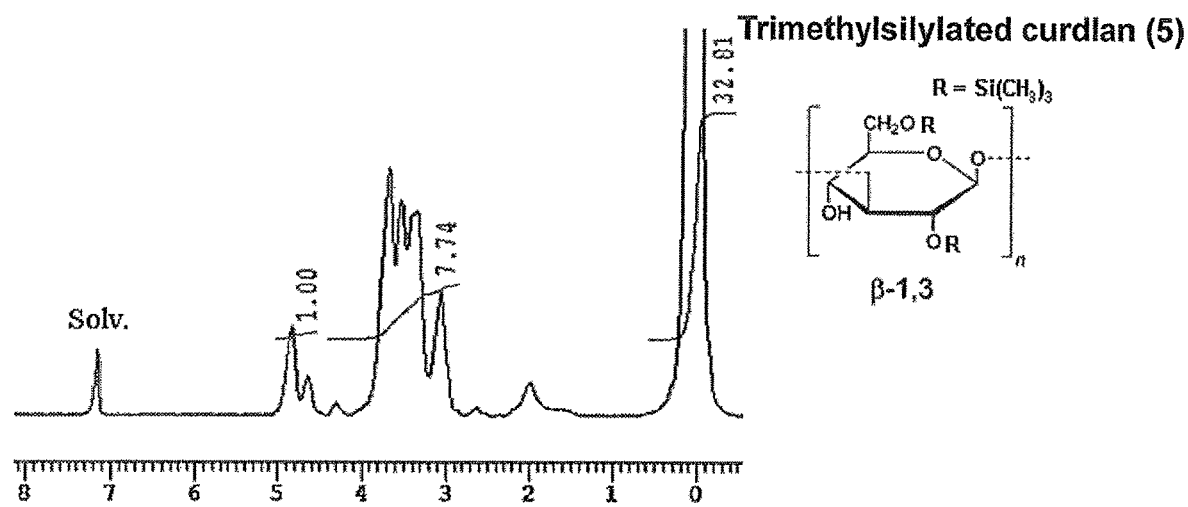
FIG. 7 shows the results of $^1$H-NMR measurement of a trimethylsilylated curdlan (5).

The progress of trimethylsilylation reaction was confirmed by $^1$H-NMR measurement (FIG. 7: trimethylsilylated curdlan (5)).

(3) Modification Reaction of Curdlan to Poly(Lactic-Co-Glycolic Acid) (Synthesis of Modified Curdlans (9) to (14))

After 0.2 g of a trimethylsilylated curdlan (5) and 14 mg of tert-butoxypotassium (tBuOK) were dried with heating under reduced pressure for 2 hours, 5 ml of tetrahydrofuran was added, followed by stirring at room temperature for 1.5 hours to obtain an activated solution. A monomer (a mixture of (DL)-lactide and glycolide with a molar ratio of 1:1) of 35-fold mol of tBuOK used for the preparation of the activated solution was dissolved in tetrahydrofuran to obtain a monomer solution. The monomer solution was added dropwise to the activated solution, followed by stirring for 30 minutes, and then 0.2 ml of acetic acid was added to stop the reaction. The solution after completion of the reaction was concentrated under reduced pressure, and reprecipitated and purified with a chloroform (good solvent)-methanol (poor solvent) system and a chloroform (good solvent)-cyclohexane (poor solvent) system to obtain a white solid. The obtained white solid was dissolved in 5 ml of chloroform, 0.4 ml of trifluoroacetic acid was added, followed by stirring at room temperature for 30 minutes. The reaction solution was concentrated under reduced pressure, and reprecipitated and purified with a chloroform (good solvent)-diethyl ether (poor solvent) system to obtain a modified curdlan (9) as a white solid.

In the same manner, a modified curdlan (10) was synthesized by reacting a trimethylsilylated curdlan (5) with a monomer of 50-fold mol of tBuOK, a modified curdlan (11) was synthesized by reacting a trimethylsilylated curdlan (6) with a monomer of 35-fold mol of tBuOK, a modified curdlan (12) was synthesized by reacting the trimethylsilylated curdlan (6) with a monomer of 50-fold mol of tBuOK, a modified curdlan (13) was synthesized by reacting a trimethylsilylated curdlan (7) with a monomer of 35-fold mol of tBuOK, and a modified curdlan (14) was synthesized by reacting the trimethylsilylated curdlan (7) with a monomer of 50-fold mol of tBuOK.

Figure 6:
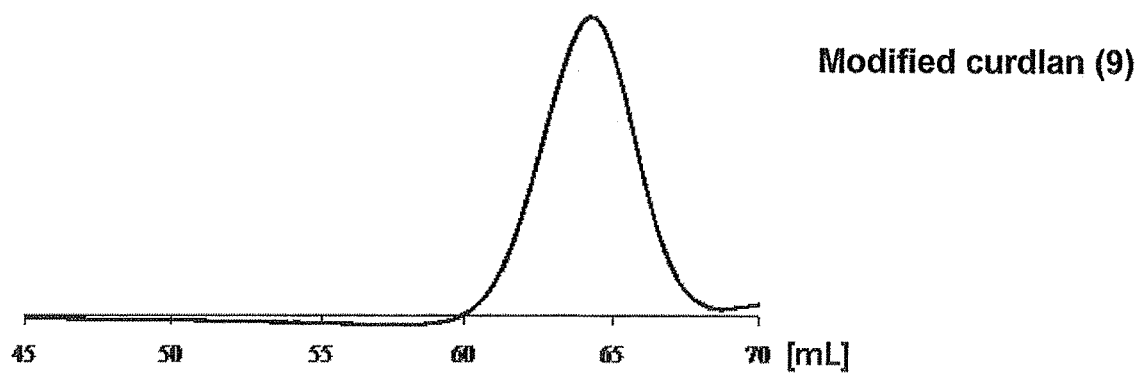
FIG. 6 shows the results of GPC measurement of a modified curdlan (9).
Figure 8:
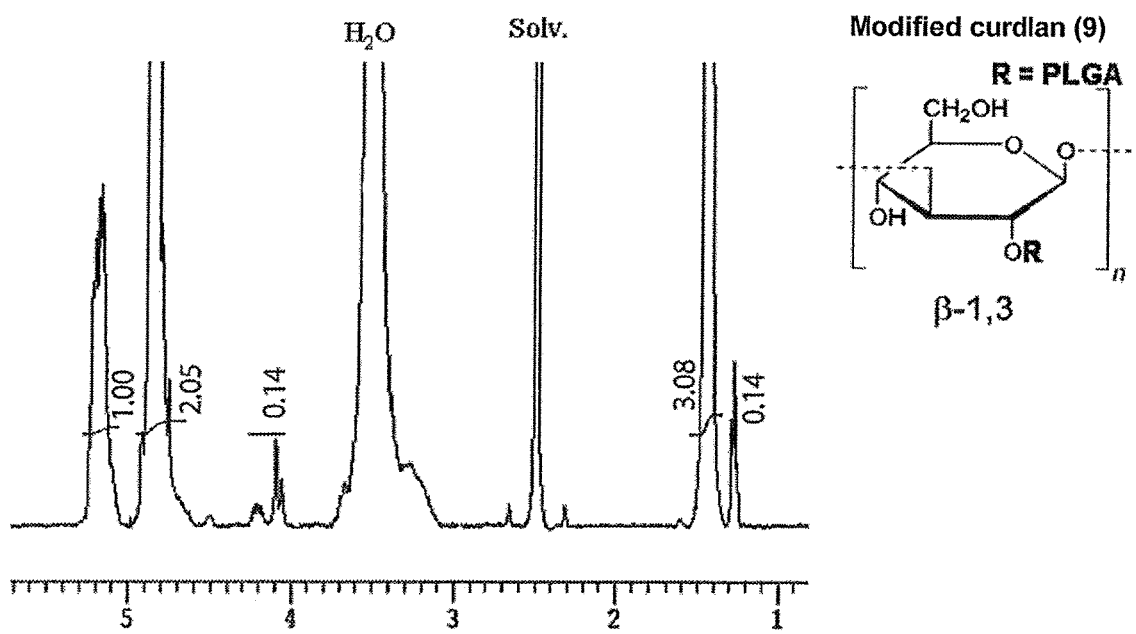
FIG. 8 shows the results of $^1$H-NMR measurement of a modified curdlan (9).

The results of assessment of modified curdlans (9) to (14) are shown in Table 2. The number average molecular weight of modified curdlan was determined by GPC measurement (column, Tosoh Corporation TSK-gel α-5000×2, DMF solvent; detector, RI; reference standard, pullulan) (FIG. 6: modified curdlan (9)). The proportion (w/w) of curdlan segments contained in the modified curdlan was determined from the number average molecular weight of curdlan used for the synthesis and the number average molecular weight of the modified curdlan. The number average molecular weight of each graft chain was determined by $^1$H-NMR measurement (FIG. 8: modified curdlan (9)). Mean number of graft chains was determined by dividing the value obtained by subtracting the number average molecular weight of curdlan from the number average molecular weight of the modified curdlan by the number average molecular weight of each graft chain.

TABLE 2

Results of analysis of modified curdlans (9) to (14)

| | Molecular weight of modified curdlan | Molecular weight of curdlan | Proportion of curdlan | Molecular weight of graft chain | Number of graft chains |
|---|---|---|---|---|---|
| Modified curdlan (9) | 18,000 | 2,800 | 15.6% | 2,500 | 6.1 |

TABLE 2-continued

Results of analysis of modified curdlans (9) to (14)

| | Molecular weight of modified curdlan | Molecular weight of curdlan | Proportion of curdlan | Molecular weight of graft chain | Number of graft chains |
|---|---|---|---|---|---|
| Modified curdlan (10) | 25,000 | | 11.2% | 4,400 | 5.0 |
| Modified curdlan (11) | 17,000 | 2,300 | 13.5% | 2,900 | 5.1 |
| Modified curdlan (12) | 22,000 | | 10.5% | 3,900 | 5.1 |
| Modified curdlan (13) | 23,000 | 1,900 | 8.3% | 3,600 | 5.9 |
| Modified curdlan (14) | 20,000 | | 9.5% | 4,900 | 3.7 |

Comparative Example 1: Synthesis of Dextran in which Poly(Lactic-Co-Glycolic Acid) is Modified (Modified Dextran (15))

Using 5 g of dextran (number average molecular weight 4,100, SERVA), 5.2 g of a trimethylsilylated dextran (8) was obtained as a white solid in the same manner as in Example 1 and Example 2 mentioned above. In the same manner as in Example 1 and Example 2 mentioned above, 0.5 g of a trimethylsilylated dextran (8) was then reacted with tert-butoxypotassium (tBuOK) and a monomer (a mixture of (DL)-lactide and glycolide with a molar ratio of 1:1) of 35-fold mol of tBuOK to obtain 0.9 g of a modified dextran (15) as a white solid.

The results of assessment of modified dextran (15) are shown in Table 3. Each value was calculated in the same manner as in Example 1 and Example 2 mentioned above.

TABLE 3

Results of analysis of modified dextran (15)

| | Molecular weight of modified dextran | Molecular weight of dextran | Proportion of dextran | Molecular weight of graft chain | Number of graft chains |
|---|---|---|---|---|---|
| Modified dextran (15) | 21,000 | 4,100 | 19.5% | 3,500 | 4.8 |

Example 3: Preparation of Particles (Curdlan Particles (1) to (5), Laminaran Particles (6) and (7), PLGA Comparative Particle (8), Dextran Comparative Particle (9)) Using the O/W Emulsion Method By dissolving 10 mg of modified curdlans (9) to (13) shown in Table 4 in 1 ml of ethyl acetate, a polymer solution was prepared. The polymer solution was added dropwise to 4 ml of a 1% (w/v) polyvinyl alcohol aqueous solution, followed by stirring at 11,000 rpm for 1 minute using a mixer (Polytron, PT2100S) to prepare an O/W emulsion solution. Ethyl acetate was removed from the O/W emulsion solution by the solvent evaporation method, and the solution was used as a particle suspension. The suspension was transferred to a 15 ml tube, and centrifuged at 8,000 rpm for 10 minutes to precipitate the particle. After the supernatant was removed, the particle was resuspended in 10 ml of distilled water, and the particle was reprecipitated by centrifugation under the above conditions. This washing operation was repeated once again, the supernatant was removed, and then the particle was suspended in 1.8 ml of an aqueous solution containing 5% (w/v) mannitol and 0.1% (w/v) polysorbate 80. The suspension was pre-frozen with liquid nitrogen, and then freeze-dried at a trap cooling temperature of −45° C. and under vacuum of 20 Pa for 12 hours using a freeze-drying device (Tokyo Rikakikai Co., Ltd., FD-1000) to obtain curdlan particles (1) to (5).

In the same manner, laminaran particles (6) and (7) with modified laminarans (3) and (8) as a base material, respectively, were obtained.

As Comparative Example, a PLGA comparative particle (8) with poly(lactic-co-glycolic acid) (PLGA, number average molecular weight 5,000, Wako Pure Chemical Industries, Ltd.) as a base material, and a dextran comparative particle (9) with modified dextran (15) as a base material were obtained in the same manner.

The mean particle size of the particle was calculated by measurement of light scattering intensity distribution and diffusion coefficient using a dynamic light scattering device (Otsuka Electronics Co., Ltd., ELS-Z) and by analysis by the cumulant method. The results are shown in Table 4.

TABLE 4

Results of analysis of particles (curdlan particles (1) to (5), laminaran particles (6) and (7), PLGA comparative particle (8), dextran comparative particle (9)) prepared by the O/W emulsion method

| | Base material | Particle size |
|---|---|---|
| Particle (1) | Modified curdlan (9) | 1024.0 nm |
| Particle (2) | Modified curdlan (10) | 1027.7 nm |
| Particle (3) | Modified curdlan (11) | 1049.6 nm |
| Particle (4) | Modified curdlan (12) | 1127.8 nm |
| Particle (5) | Modified curdlan (13) | 1026.2 nm |
| Particle (6) | Modified laminaran (3) | 1270.0 nm |
| Particle (7) | Modified laminaran (8) | 1059.0 nm |
| Comparative particle (8) | Poly(lactic-co-glycolic acid) | 1095.3 nm |
| Comparative particle (9) | Modified dextran (15) | 957.9 nm |

Example 4: Preparation of Particles (Curdlan Particle Containing OVA (10), Curdlan Particle (11), Laminaran Particles Containing OVA (12) to (14), Dextran Comparative Particle Containing OVA (15)) Using the S/O/W Emulsion Method By dissolving 100 mg of modified curdlan (13) in 1.8 ml of dimethyl carbonate and 200 µl of tert-butanol, a polymer solution was prepared. To the polymer solution, 1 ml of a 0.1% (w/v) OVA (ovalbumin, Sigma-Aldrich Co. LLC.) aqueous solution was added dropwise, followed by stirring at 11,000 rpm for 1 minute using a mixer (Polytron, PT2100S) to prepare a W/O emulsion solution. The W/O emulsion solution was pre-frozen with liquid nitrogen, and then freeze-dried for 12 hours at a trap cooling temperature of −45° C. and under vacuum of 20 Pa using a freeze-drying device (Tokyo Rikakikai Co., Ltd., FD-1000). The obtained solid contents were dispersed in 10 ml of ethyl acetate to prepare an S/O suspension solution. The S/O suspension solution was added dropwise to 40 ml of 1% (w/v) polyvinyl alcohol aqueous solution, followed by stirring at 6,000 rpm for 5 minutes using a mixer (Silverson Nippon Ltd, L5M-A)

to prepare an S/O/W emulsion solution. Ethyl acetate was removed from the S/O/W emulsion solution by the solvent evaporation method, and the solution was used as a particle suspension. The suspension was transferred to a 50 ml tube, and centrifuged at 8,000 rpm for 10 minutes to precipitate the particle. After the supernatant was removed, the particle was resuspended in 50 ml of distilled water, and the particle was reprecipitated by centrifugation under the above conditions. This washing operation was repeated once again, the supernatant was removed, and then the particle was suspended in 8 ml of an aqueous solution containing 5% (w/v) mannitol and 0.1% (w/v) polysorbate 80. The suspension was pre-frozen with liquid nitrogen, and then freeze-dried for 12 hours at a trap cooling temperature of −45° C. and under vacuum of 20 Pa using a freeze-drying device to obtain a curdlan particle containing OVA (10).

Using distilled water instead of OVA solution, a curdlan particle not containing OVA (11), was obtained in the same manner. Using modified laminarans (1), (3), and (5), laminaran particles containing OVA (12) to (14) were obtained in the same manner.

As Comparative Example, using modified dextran (15) as a base material, dextran comparative particle containing OVA (15) was obtained in the same manner.

The results of assessment of particles are shown in Table 5. The mean particle size of particles was calculated by the cumulant method using a dynamic light scattering device (Otsuka Electronics Co., Ltd., ELS-Z). The encapsulation rate (w/w) of an antigen was determined by extracting the antigen from the particle using an organic solvent, by performing gel electrophoresis for the extracted antigen using a gel electrophoresis device (TEFCO), and then by staining the antigen using a colloid CBB staining kit (TEFCO).

TABLE 5

Results of analysis of particles (curdlan particle containing OVA (10), curdlan particle (11), laminaran particles containing OVA (12) to (14), dextran comparative particle containing OVA (15)) prepared by the S/O/W emulsion method

|  | Base material | Particle size | Encapsulation rate of antigen |
| --- | --- | --- | --- |
| Particle (10) | Modified curdlan (13) | 483.9 nm | 0.96% |
| Particle (11) | Modified curdlan (13) | 484.4 nm | — |
| Particle (12) | Modified laminaran (1) | 508.0 nm | 0.94% |
| Particle (13) | Modified laminaran (3) | 556.3 nm | 0.93% |
| Particle (14) | Modified laminaran (5) | 517.9 nm | 0.85% |
| Comparative particle (15) | Modified dextran (15) | 537.2 nm | 0.89% |

Reference Example 1: Induction of Murine Bone Marrow-Derived Dendritic Cells (BMDC)

After 8-week old male C57BL/6 mice were euthanized with carbonic acid gas, the femur was removed. Both ends of the femur was cut with scissors, an RPMI1640 medium (hereinafter referred to as RPMI medium) containing 10% FBS (Sigma-Aldrich Co. LLC.), 100 IU/ml penicillin (Life Technologies, Inc.), and 100 IU/ml streptomycin (Life Technologies, Inc.) was injected into the inside of the femur with an injector, and a bone marrow solution was collected. The bone marrow solution was centrifuged at 1,500 rpm for 5 minutes to precipitate the cells, and the supernatant was removed. The collected cells were suspended in 1 ml of a hemolysis buffer (1.66% [w/v] ammonium chloride aqueous solution), and then allowed to stand at 4° C. for 4 minutes to hemolyze the cells. To the cell suspension after hemolysis, 10 ml of an RPMI medium was added, the solution was centrifuged at 1,500 rpm for 5 minutes to precipitate the cells, and the supernatant was removed. The cells were suspended in an RPMI1640 medium (hereinafter referred to as culture medium) containing 10% FBS (Sigma-Aldrich Co. LLC.), 10 ng/ml GM-CSF, 100 IU/ml penicillin (Life Technologies, Inc.), and 100 IU/ml streptomycin (Life Technologies, Inc.), and then seeded on a 6-well plate (IWAKI & Co., Ltd., Flat Bottom Tissue culture Treated, Polystyrene). The seeded plate was incubated for 3 hours in a $CO_2$ incubator (NAPCO) under the conditions of 5% $CO_2$, 37° C., and humidity 100%, and the cells were strongly suspended using a micropipette to collect only cells not adhered on the plate. The collected cells were resuspended in a culture medium, and then seeded on a 6-well plate and incubated in a $CO_2$ incubator. The culture medium was exchanged on days 2 and 4 of culture, and the cells were strongly suspended using a micropipette on day 5 of culture to collect only cells not adhered on the plate, namely, induced dendritic cells.

Example 5: In Vitro Stimulation Test of Modified β-Glucan in Murine Bone Marrow-Derived Dendritic Cells (BMDC)

<Methods>

After weighing 10 mg of the modified β-glucan obtained in Example 2 (modified curdlans (9) to (12)), the modified β-glucan was dissolved in 10 ml of acetonitrile to obtain a polymer solution. By dropping 100 μl of the polymer solution (100 μg of polymer) into a 6-well plate and drying the plate, a polymer coated plate was obtained. On the polymer coated plate, the dendritic cells obtained in Reference Example 1 were seeded together with a culture medium so that the number of cells was 1×10⁶ per well. The seeded plate was incubated for 2 days in a $CO_2$ incubator, and then the cells were strongly suspended using a micropipette to collect only cells not adhered on the plate. The collected cells were centrifuged at 1,500 rpm for 5 minutes to precipitate the cells, the supernatant was removed, and the cells were suspended in 100 μl of an RPMI medium. To the cell suspension, FITC-labeled anti-CD86 antibodies and PE-labeled anti-CD11c antibodies were added, and the suspension was allowed to stand at 4° C. for 15 minutes to perform antibody labeling reaction. After completion of the antibody labeling reaction, the expression level of an activation marker (CD86) was assessed based on mean fluorescence intensity (MFI) by flow cytometry.

As Comparative Example, using a plate on which modified dextran (15) obtained in Comparative Example 1, a trimethylsilylated curdlan (1) obtained in Example 1, or poly(lactic-co-glycolic acid) (PLGA, Wako Pure Chemical Industries, Ltd., PLGA-5020) was coated in the same manner, and the expression level of the activation marker was compared in the same manner. As another Comparative Example, 100 μg of curdlan hydrolysate (1) obtained in Example 1 or 100 μg of poly I:C (Sigma-Aldrich Co. LLC.) with known immunopotentiating capacity was added to a culture medium, and the expression level of the activation marker was compared in the same manner.

<Results>

Figure 9:
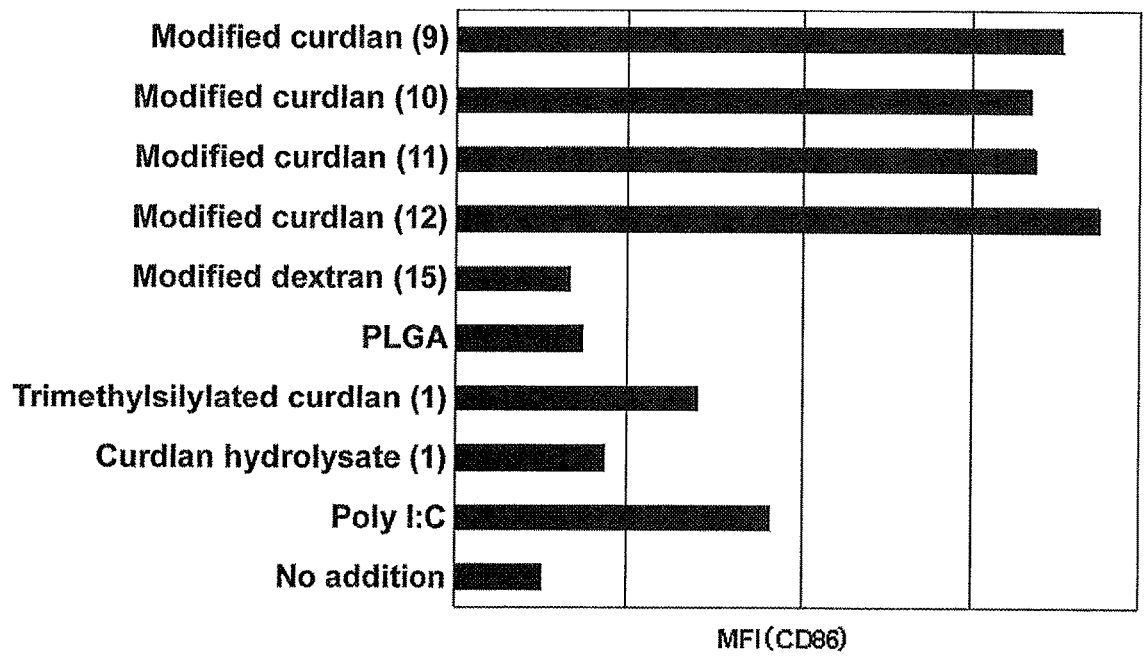
FIG. 9 shows the results of in vitro stimulation test of a modified β-glucan.

Mean fluorescence intensity (MFI), an index of the expression level of CD86, is shown in FIG. 9. CD86 is one of the activation markers of dendritic cells. When modified curdlans (9) to (12) were used, the expression level of CD86 was higher than that when modified dextran (15) and poly (lactic-co-glycolic acid) were used, revealing that modified β-glucan has potent dendritic cell activation capacity. When a curdlan hydrolysate (1) and a trimethylsilylated curdlan (1) were used, the expression level of CD86 was lower than that when modified β-glucan was used, revealing that modification of poly(hydroxy acid) to β-glucan is important for activation of dendritic cells.

Example 6: In Vitro Stimulation Test 1 of Particles with Modified β-Glucan as a Base Material in Murine Bone Marrow-Derived Dendritic Cells (BMDC)

<Methods>

The dendritic cells obtained in Reference Example 1 were seeded together with a culture medium on a 6-well plate so that the number of cells was $1\times10^6$ per well, and 0.2 mg of the particles prepared in Example 3 (curdlan particles (1) to (5), PLGA comparative particle (8), dextran comparative particle (9)) were further added. The seeded plate was incubated for 2 days in a $CO_2$ incubator, and then the cells were strongly suspended using a micropipette to collect only cells not adhered on the plate. The collected cells were centrifuged at 1,500 rpm for 5 minutes to precipitate the cells, the supernatant was removed, and the cells were suspended in 100 μl of an RPMI medium. To the cell suspension, FITC-labeled anti-CD86 antibodies and PE-labeled anti-CD11c antibodies were added, and the suspension was allowed to stand at 4° C. for 15 minutes to perform antibody labeling reaction. After completion of the antibody labeling reaction, the expression level of an activation marker (CD86) was assessed based on mean fluorescence intensity (MFI) by flow cytometry.

As Comparative Example, 100 μg of poly I:C (Sigma-Aldrich Co. LLC.) was added to a culture medium, and the expression level of the activation marker was compared in the same manner.

<Results>

Figure 10:
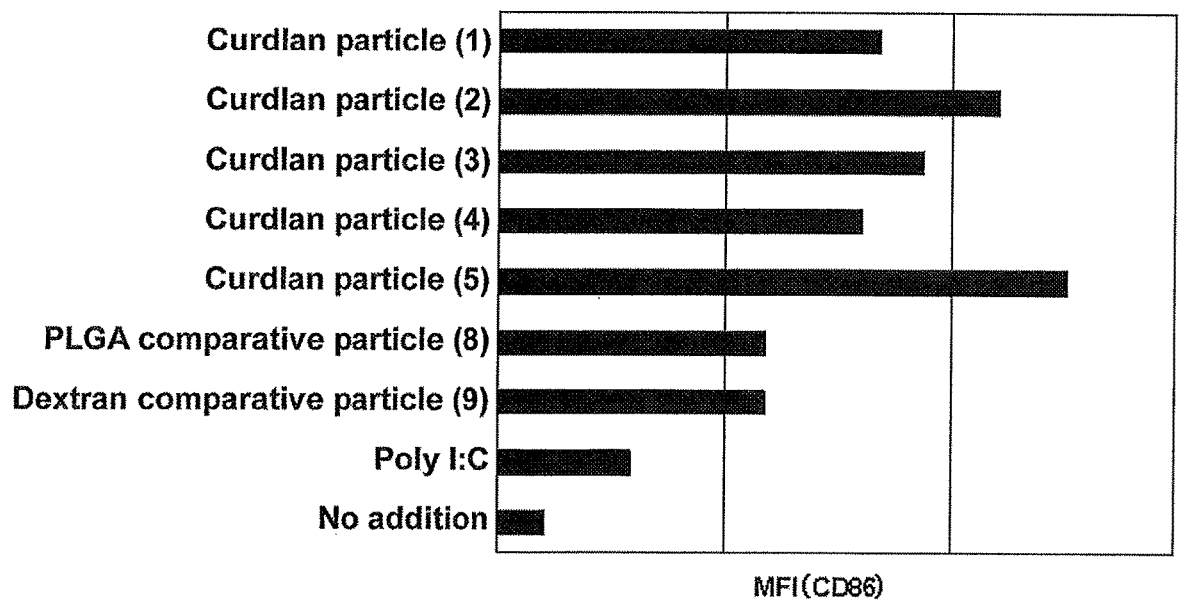
FIG. 10 shows the results of in vitro stimulation test 1 of particles with a modified β-glucan as a base material.

Mean fluorescence intensity (MFI), an index of the expression level of CD86 in each particle, is shown in FIG. 10. When particles (curdlan particles (1) to (5), PLGA comparative particle (8), dextran comparative particle (8)) were used, the expression level of CD86 was higher than that when no particles were added, revealing that particles have dendritic cell activation capacity. Furthermore, when particles with modified curdlan as a base material (curdlan particles (1) to (5)) were used, they were revealed to have more potent dendritic cell activation capacity than a particle with modified dextran as a base material (dextran comparative particle (9)) or particle with PLGA as a base material (PLGA comparative particle (8)). Particles with modified β-glucan as a base material were found to have potent immunopotentiating capacity.

Example 7: In Vitro Stimulation Test 2 of Particles with Modified β-Glucan as a Base Material in Murine Bone Marrow-Derived Dendritic Cells (BMDC)

<Methods>

In the same manner as in Example 6, 0.2 mg of the particles prepared in Example 3 (laminaran particles (6) and (7), PLGA comparative particle (8), dextran comparative particle (9)) was added on a plate on which the dendritic cells obtained in Reference Example 1 were seeded, and the expression level of an activation marker (CD86) was assessed based on mean fluorescence intensity (MFI).

As Comparative Example, 100 μg of poly I:C (Sigma-Aldrich Co. LLC.) was added to a culture medium, and the expression level of the activation marker was compared in the same manner.

<Results>

Figure 11:
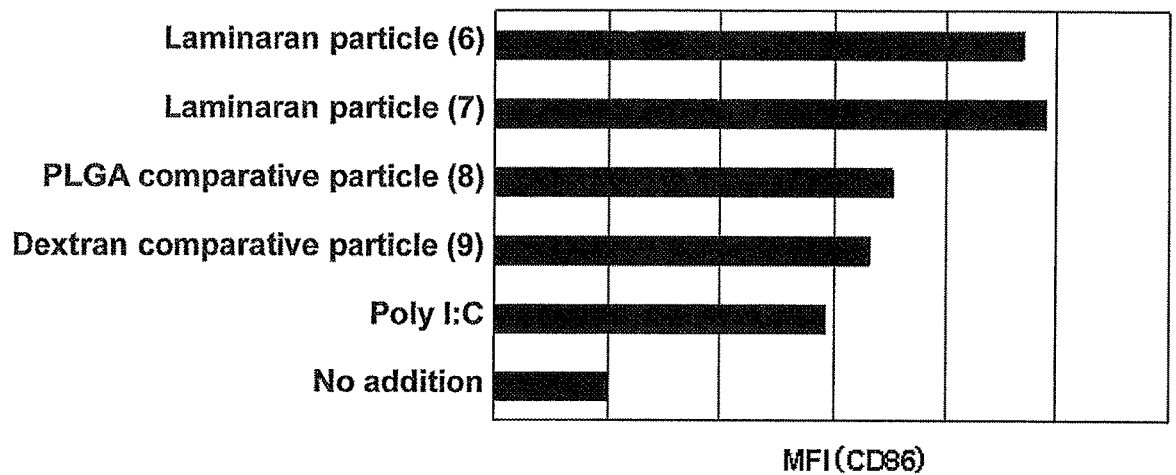
FIG. 11 shows the results of in vitro stimulation test 2 of particles with a modified β-glucan as a base material.

Mean fluorescence intensity (MFI), an index of the expression level of CD86 in each particle, is shown in FIG. 11. When particles with modified laminaran as a base material (laminaran particles (6) and (7)) were used, they were revealed to have more potent dendritic cell activation capacity than a particle with modified dextran as a base material (dextran comparative particle (9)) or a particle with PLGA as a base material (PLGA comparative particle (8)). In other words, particles with modified laminaran as a base material were revealed to have potent dendritic cell activation capacity, like particles with modified curdlan as a base material in Example 6.

Example 8: In Vivo Test 1 of Modified β-Glucan in Mice (Assessment by IFN-γ Production Capacity)

<Methods>

Mice used for the experiment were 5-week male C57BL/6NCR mice purchased from Japan SLC, Inc. The mice were raised under free-feeding conditions with a 12-hour day/night cycle at an in-house rearing facility for 1 week and acclimated to the environment.

Administration was performed to the mice under the conditions shown in Table 6. Under conditions (1) and (2) and comparative condition (3), the particles prepared in Example 4 (curdlan particle containing OVA (10), dextran comparative particle containing OVA (15)) were dispersed in 50 μl of 4% (w/v) mannitol aqueous solution, and the solution was administered to foot pads on both hind legs using a 29G injection needle (Terumo Myjector). Under comparative condition (4), OVA (Sigma-Aldrich Co. LLC.) and poly I:C (Sigma-Aldrich Co. LLC.) were administered in the same manner. Under comparative condition (5), a solution not containing antigens was administered in the same manner.

Under condition (2) and comparative conditions (3) and (4), the second administration was performed 3 days after the first administration in the same manner, and the third administration was performed 6 days after the first administration in the same manner.

The mice after administration were raised under free-feeding conditions and an environment where water supply is possible, and euthanized with carbonic acid gas 2 weeks after the first administration. Lymph nodes below the knee near the administration site were aseptically removed, the contained cells were dispersed, and then filtered with a 200 μm filter (AS ONE Corporation, FILCONS, 120-22S) to remove debris. The collected cells were suspended in an RPMI1640 medium (hereinafter referred to as RPMI medium) containing 10% FBS (Sigma-Aldrich Co. LLC.), 100 IU/ml penicillin (Life Technologies, Inc.), and 100 IU/ml streptomycin (Life Technologies, Inc.), seeded on a 96-well plate (IWAKI & Co., Ltd., Flat Bottom Tissue Culture Polystyrene) so that the number of cells was $5\times10^5$ per well, and an RPMI medium containing 10 μg of OVA and 0.75 μg of 2-mercaptoethanol was further added to stimulate the cells. The seeded plate was incubated in a $CO_2$ incubator for 48 hours, the culture supernatant was collected, and the concentration of IFN-γ produced from each cell group was measured by the ELISA method (Mabtech AB, Mouse IFN-gamma ELISA kit [HRP]).

<Results>

Figure 12:
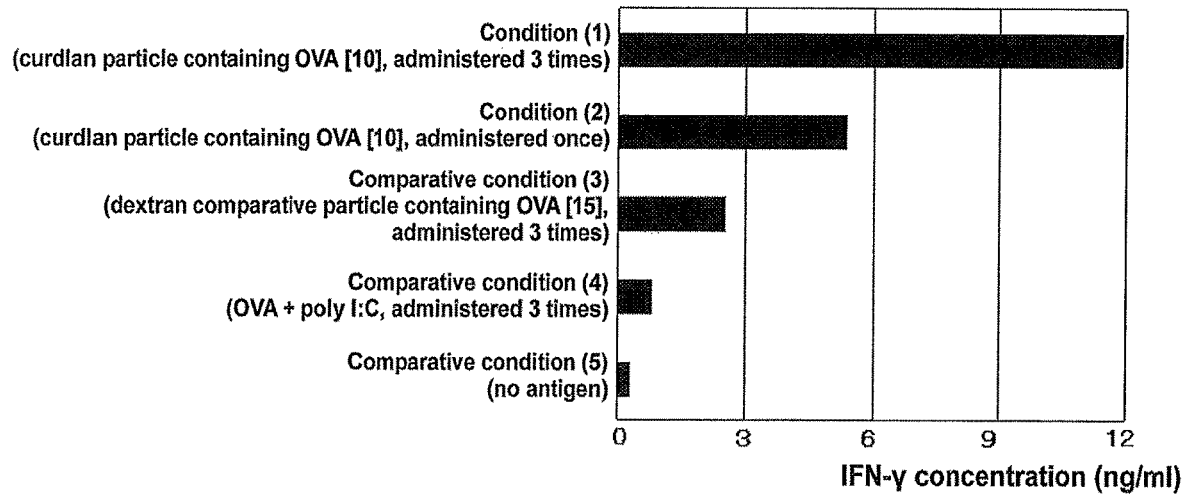
FIG. 12 shows the results of in vivo test 1 of a modified β-glucan.

The amount of IFN-γ produced by lymph node cells is shown in FIG. 12. IFN-γ is an index of activation of cell-mediated immunity. Under the conditions in which a particle containing OVA was administered (conditions (1) and (2) and comparative condition (3)), stronger production of IFN-γ was found than under the condition in which an antigen was not administered (comparative condition (5)) and the condition in which OVA and poly I:C were administered (comparative condition (4)), revealing that a particle containing an antigen is effective for activation of antigen-specific immunity. Under the conditions in which a particle with modified curdlan as a base material was administered (conditions (1) and (2)), more stronger production of IFN-γ was found than under the condition in which a particle with modified dextran as a base material was administered (comparative condition (3)). In other words, a particle with modified β-glucan as a base material and containing an antigen was revealed to enhance antigen-specific immunity. Under the condition in which a particle was administered 3 times (condition (2)), higher production of IFN-γ was found than under the condition in which the particle was administered once (condition (1)), revealing that multiple administration is also effective for further enhancement of immunity.

TABLE 6

Administration conditions in in vivo test 1 of modified β-glucan in mice

| | Substance administered | Frequency of administration |
|---|---|---|
| Condition (1) | 2.5 mg of curdlan particle containing OVA (10) | 1 |
| Condition (2) | 2.5 mg of curdlan particle containing OVA (10) | 3 |
| Comparative condition (3) | 2.5 mg of dextran comparative particle containing OVA (15) | 3 |
| Comparative condition (4) | 25 μg of OVA, 25 μg of poly I:C | 3 |
| Comparative condition (5) | — | 1 |

Example 9: In Vivo Test 2 of Modified β-Glucan in Mice (Assessment by IFN-γ Production Capacity)

<Methods>

Administration was performed under the conditions shown in Table 7 to mice raised under the same conditions as in Example 8. Under conditions (6) to (8) and comparative condition (9), the particles prepared in Example 4 (laminaran particles containing OVA (12) to (14), dextran comparative particle containing OVA (15)) were dispersed in 100 μl of 4% (w/v) mannitol aqueous solution, and the solution was administered to foot pads on both hind legs using a 29G injection needle (Terumo Myjector). Under comparative condition (10), OVA (Sigma-Aldrich Co. LLC.) and poly I:C (Sigma-Aldrich Co. LLC.) were administered in the same manner. Under comparative condition (11), OVA (Sigma-Aldrich Co. LLC.) was administered in the same manner. Under comparative condition (12), a solution not containing antigens was administered in the same manner.

The mice after administration were raised under free-feeding conditions and an environment where water supply is possible, and euthanized with carbonic acid gas 2 weeks after the first administration. In the same manner as in Example 8, cells contained in the lymph nodes were removed, and the production amount of IFN-γ after stimulation with OVA was measured.

<Results>

Figure 13:
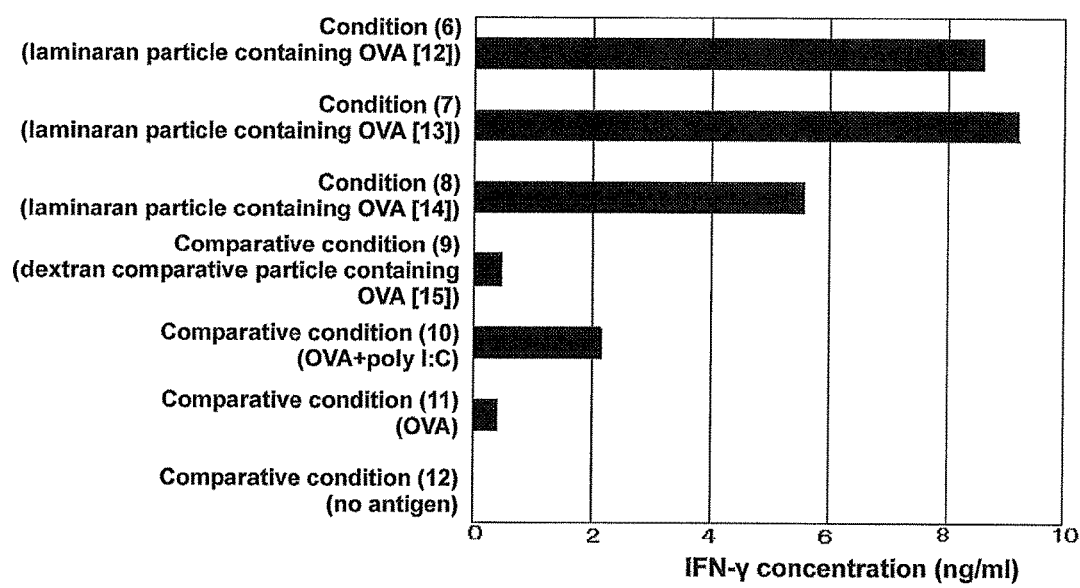
FIG. 13 shows the results of in vivo test 2 of a modified β-glucan.

The amount of IFN-γ produced by lymph node cells is shown in FIG. 13. Under the conditions in which laminaran particles containing OVA were administered (conditions (6) to (8)), stronger production of IFN-γ was observed than under the condition in which dextran comparative particle containing OVA was administered (comparative condition (9)) and the condition in which OVA and poly I:C were administered (comparative condition (10]). Like a particle with modified curdlan as a base material and containing an antigen in Example 8, a particle with modified laminaran as a base material and containing an antigen was revealed to enhance antigen-specific immunity.

TABLE 7

Administration conditions in in vivo test 2 of modified β-glucan in mice

| | Substance administered | Frequency of administration |
|---|---|---|
| Condition (6) | 5 mg of laminaran particle containing OVA (12) | 1 |
| Condition (7) | 5 mg of laminaran particle containing OVA (13) | 1 |
| Condition (8) | 5 mg of laminaran particle containing OVA (14) | 1 |
| Comparative condition (9) | 5 mg of dextran comparative particle containing OVA (15) | 1 |
| Comparative condition (10) | 50 μg of OVA, 50 μg of poly I:C | 1 |
| Comparative condition (11) | 50 μg of OVA | 1 |
| Comparative condition (12) | — | 1 |

Example 10: In Vivo Test 3 of Modified β-Glucan in Mice (Antitumor Effects)

<Methods>

Using OVA-expressing murine cancer cells E.G7-OVA (ATCC) as tumor-bearing cells, a logarithmic growth state was kept in advance, and the cells were cultured for 1 week with an RPMI medium. Then, the cells were washed 3 times with sterilized PBS to prepare cells to be transplanted.

As host animals, 5-week old male C57BL/6NCR mice purchased from Japan SLC, Inc. were raised under free-feeding conditions with a 12-hour day/night cycle at our rearing facility and acclimated to the environment. Then, 100 μl of PBS containing $2 \times 10^6$ E.G7-OVA cells was subcutaneously administered to the abdomen using a 25G injection needle to develop a tumor.

On days 0, 3, 7, 10, and 15 after development of a tumor, administration was performed to the mice under the conditions shown in Table 8. Under conditions (13) and (14), the particles prepared in Example 4 (curdlan particle containing OVA (10), curdlan particle (11)) were dispersed in 100 μl of 4% (w/v) mannitol aqueous solution, and the solution was administered to the vicinity of the tumor-bearing site using a 29G injection needle (Terumo Myjector). Under comparative condition (15), OVA (Sigma-Aldrich Co. LLC.) and poly I:C (Sigma-Aldrich Co. LLC.) were administered in the same manner. Under comparative condition (16), a solution not containing antigens nor particles was administered in the same manner.

The mice after administration were raised under free-feeding conditions and an environment where water supply is possible, and the volume of the tumor tissue was measured.

<Results>

Figure 14:
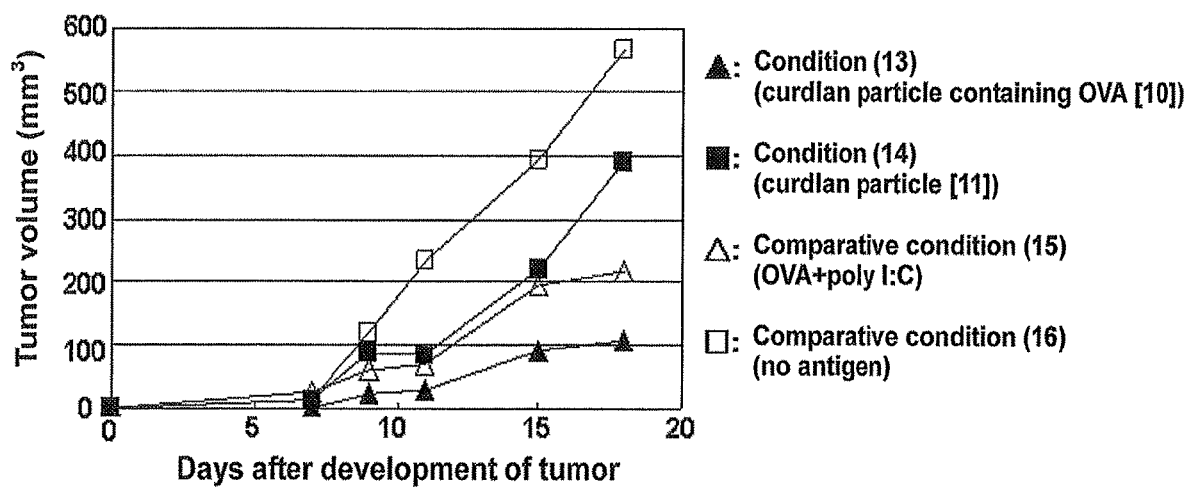
FIG. 14 shows the results of in vivo test 3 of a modified β-glucan.

Mean volume of the tumor tissue in 5 mice after development of a tumor under each condition is shown in FIG. 14. Under the condition in which a particle not containing antigens was administered (condition (14)), increase in tumor volume was more suppressed than under the condition in which neither antigens nor particles were administered (comparative condition (16)), revealing that a particle with modified β-glucan as a base material has antitumor effects. Under the condition in which a particle containing an antigen was administered (13), increase in tumor volume was more suppressed than under the condition in which a particle not containing antigens was administered (condition (14)) and the condition in which OVA and poly I:C were administered (comparative condition (15)), revealing that a particle with modified β-glucan as a base material and containing an antigen has more potent antitumor effects.

TABLE 8

Administration conditions in in vivo test 3 of modified β-glucan in mice

| | Substance administered | Frequency of administration |
| --- | --- | --- |
| Condition (13) | 5 mg of curdlan particle containing OVA (10) | 5 |
| Condition (14) | 5 mg of curdlan particle (11) | 5 |
| Comparative condition (15) | 50 ug of OVA, 50 μg of poly I:C | 5 |
| Comparative condition (16) | — | 5 |

Example 11: Synthesis of β-Glucan in which Poly (Lactic-Co-Glycolic Acid) is Modified (Modified Pachyman (16), Modified Sizofiran (17), Modified Aureobasidium pullulans Glucan (18), Modified Scleroglucan (19), Modified Curdlans (20) and (21))

(1) Hydrolysis Reaction of β-Glucan (Synthesis of Pachyman Hydrolysate (7), Sizofiran Hydrolysate (8), Aureobasidium pullulans Glucan Hydrolysate (9), Scleroglucan Hydrolysate (10), Curdlan Hydrolysates (11) and (12))

After 320 mg of pachyman (Bio Supply) was dissolved in 27 ml of dimethyl sulfoxide, 1.2 ml of 1 N hydrochloric acid solution was added, followed by stirring at 110° C. for 0.5 hour. The reaction solution was transferred to a dialysis membrane and dialyzed in water, and then freeze-dried to obtain pachyman hydrolysate (7) (number average molecular weight 1,900) as a powder.

Under the same conditions, a sizofiran hydrolysate (8) (number average molecular weight 4,400) was obtained by reaction of sizofiran (InvivoGen) for 1.3 hours, Aureobasidium pullulans glucan hydrolysate (9) (number average molecular weight 2,700) was obtained by reaction of Aureobasidium pullulans glucan (DAISO Co., Ltd.) for 0.15 hours, scleroglucan hydrolysate (10) (number average molecular weight 3,000) was obtained by reaction of scleroglucan (Ethycythyl) for 1.15 hours, and a curdlan hydrolysate (11) (number average molecular weight 18,700) and a curdlan hydrolysate (12) (number average molecular weight 1,900) were obtained by reaction of curdlan (Wako Pure Chemical Industries, Ltd.) for 0.1 hour and 0.75 hour, respectively.

The number average molecular weight of β-glucan was determined by GPC measurement (column, Tosoh Corporation TSK-gel G3000PW$_{XL}$-CP×2, acetic acid buffer solvent [10 mM, pH=5], detector, RI; reference standard, pullulan).

(2) Trimethylsilylation (TMS) Reaction of β-Glucan (Synthesis of Trimethylsilylated Pachyman (9), Trimethylsilylated Sizofiran (10), Trimethylsilylated Aureobasidium pullulans Glucan (11), Trimethylsilylated Scleroglucan (12), Trimethylsilylated Curdlan (13) and (14))

After 180 mg of a pachyman hydrolysate (7) was added to 25 ml of dimethyl sulfoxide, the solution was heated to 80° C. To this solution, 20 ml of 1,1,1,3,3,3-hexamethyldisilazane was added dropwise over 20 minutes, followed by stirring at 80° C. for 16 hours. The reaction solution was transferred to a separatory funnel, and allowed to stand until it is separated to two layers. The upper layer was collected and concentrated under reduced pressure and 5 ml of methanol was added, and then the obtained solid was filtered and dried to obtain 250 mg of a trimethylsilylated pachyman (9) as a white solid.

In the same manner, a trimethylsilylated sizofiran (10) was synthesized from a sizofiran hydrolysate (8), a trimethylsilylated Aureobasidium pullulans glucan (11) was synthesized from an Aureobasidium pullulans glucan hydrolysate (9), a trimethylsilylated scleroglucan (12) was synthesized from scleroglucan hydrolysate (10), a trimethylsilylated curdlan (13) was synthesized from a curdlan hydrolysate (11), and a trimethylsilylated curdlan (14) was synthesized from a curdlan hydrolysate (12).

The progress of trimethylsilylation reaction was confirmed by $^1$H-NMR measurement.

(3) Modification Reaction of Poly(Lactic-Co-Glycolic Acid) to β-Glucan (Synthesis of Modified Pachyman (16), Modified Sizofiran (17), Modified Aureobasidium pullulans Glucan (18), Modified Scleroglucan (19), Modified Curdlan (20) and (21))

After 230 mg of a trimethylsilylated pachyman (9) and 22 mg of tert-butoxypotassium (tBuOK) were dried with heating under reduced pressure for 2 hours, 10 ml of tetrahydrofuran was added, followed by stirring at room temperature for 1.5 hours to obtain an activated solution. A monomer (a mixture of (DL)-lactide and glycolide with a molar ratio of 1:1) of 35-fold mol of tBuOK used for the preparation of the activated solution was dissolved in tetrahydrofuran to obtain a monomer solution. The monomer solution was added dropwise to the activated solution, followed by stirring for 30 minutes, and then 0.2 ml of acetic acid was added to stop the reaction. The solution after completion of the reaction was concentrated under reduced pressure, and reprecipitated and purified with a chloroform (good solvent)-methanol (poor solvent) system and a chloroform (good solvent)-cyclohexane (poor solvent) system to obtain a white solid. The obtained white solid was dissolved in 9 ml of chloroform, 1 ml of trifluoroacetic acid was added, followed by stirring at room temperature for 30 minutes. The reaction solution was concentrated under reduced pressure, and reprecipitated and purified with a chloroform (good solvent)-diethyl ether (poor solvent) system to obtain 287 mg of a modified pachyman (16) as a white solid.

In the same manner, a modified sizofiran (17) was synthesized from a trimethylsilylated sizofiran (10), a modified Aureobasidium pullulans glucan (18) was synthesized from a trimethylsilylated Aureobasidium pullulans glucan (11), a modified scleroglucan (19) was synthesized from a trimethylsilylated scleroglucan (12), a modified curdlan (20) was synthesized from a trimethylsilylated curdlan (13), and a modified curdlan (21) was synthesized from a trimethylsilylated curdlan (14)

Figure 15:
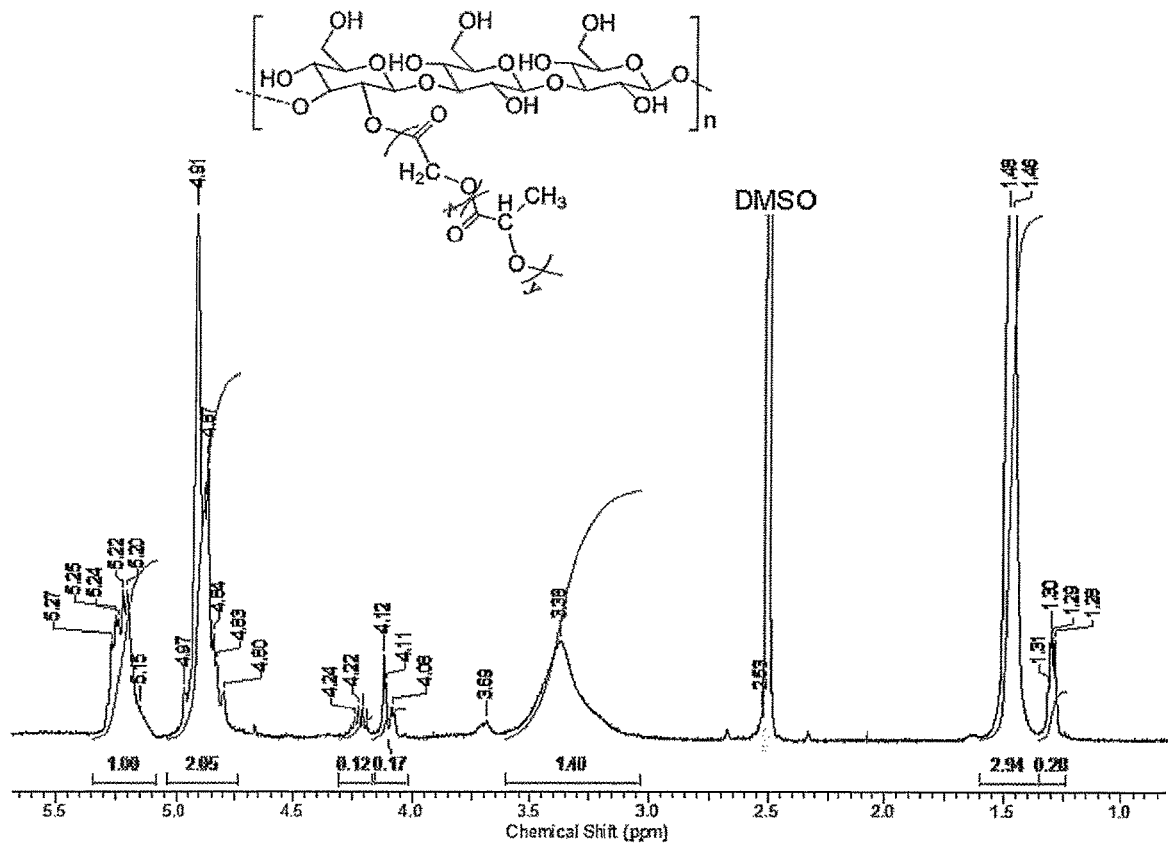
FIG. 15 shows the results of $^1$H-NMR measurement of modified pachyman (16).
Figure 16:
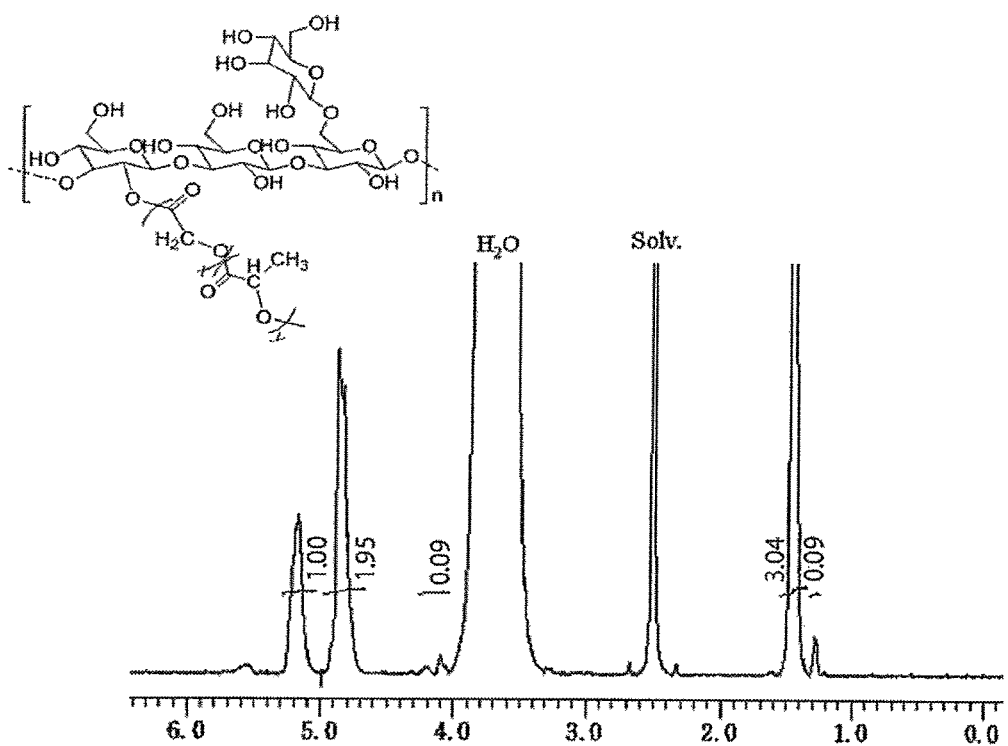
FIG. 16 shows the results of $^1$H-NMR measurement of a modified sizofiran (17).
Figure 17:
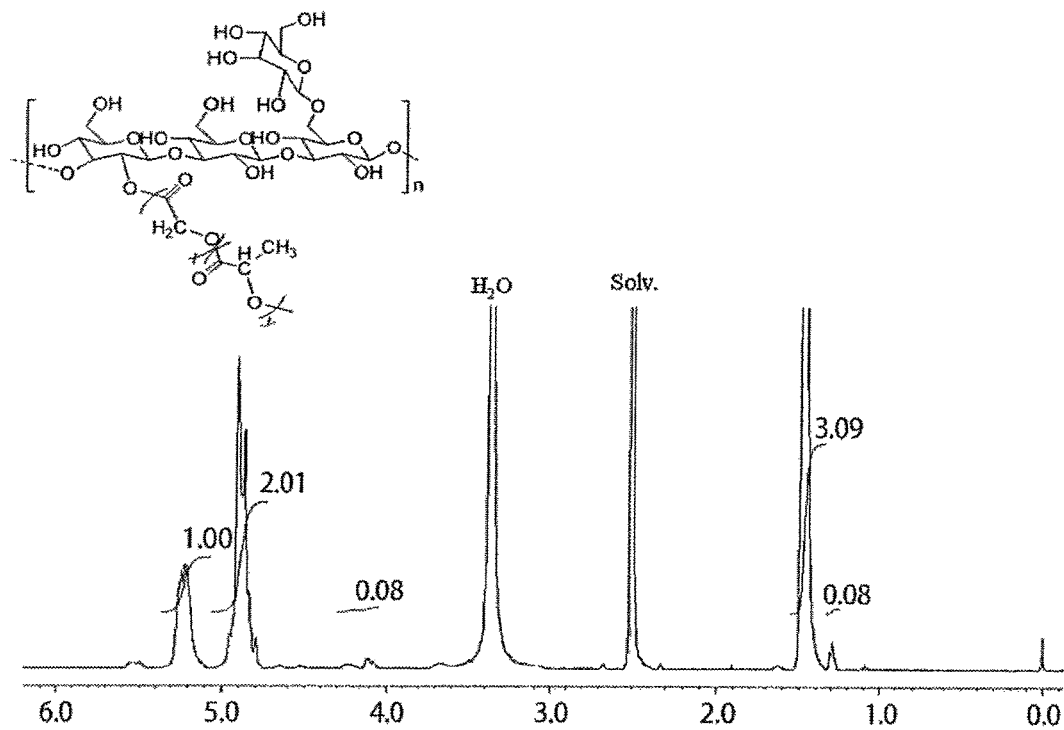
FIG. 17 shows the results of $^1$H-NMR measurement of a modified *Aureobasidium pullulans* glucan (18).
Figure 18:
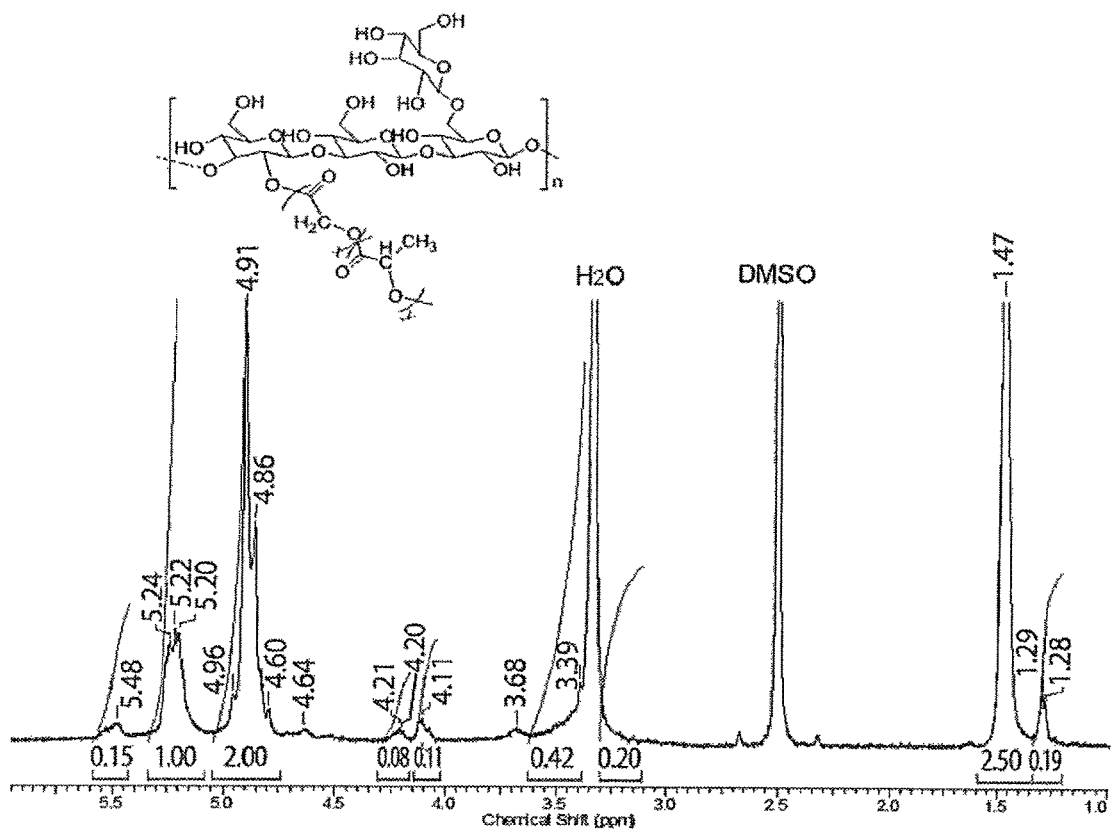
FIG. 18 shows the results of $^1$H-NMR measurement of a modified scleroglucan (19).

The results of assessment of modified β-glucan are shown in Table 9. The number average molecular weight of modified β-glucan was determined by GPC measurement (column, Tosoh Corporation TSK-gel α-5000×2, DMF solvent; detector, RI; reference standard, pullulan). The proportion (w/w) of β-glucan segments contained in modified β-glucan was determined from the number average molecular weight of β-glucan used for the synthesis and the number average molecular weight of modified β-glucan. The number average molecular weight of each graft chain was determined by $^1$H-NMR measurement (FIG. 15, modified pachyman (16); FIG. 16, modified sizofiran (17); FIG. 17, modified *Aureobasidium pullulans* glucan (18); FIG. 18, modified scleroglucan (19)). Mean number of graft chains was determined by dividing the value obtained by subtracting the number average molecular weight of β-glucan from the number average molecular weight of modified β-glucan by the number average molecular weight of each graft chain.

TABLE 9

Results of analysis of modified β-glucans (modified pachyman (16), modified sizofiran (17), modified *Aureobasidium pullulans* glucan (18), modified scleroglucan (19), modified curdlan (20) and (21))

| | Molecular weight of modified β-glucan | Molecular weight of β-glucan | Proportion of β-glucan | Molecular weight of graft chain | Number of graft chains |
|---|---|---|---|---|---|
| Modified pachyman (16) | 13,800 | 1,900 | 13.8% | 1,300 | 9.2 |
| Modified sizofiran (17) | 14,700 | 4,400 | 29.9% | 4,200 | 2.5 |
| Modified *Aureobasidium pullulans* β-glucan(18) | 15,100 | 2,700 | 17.9% | 4,900 | 2.5 |
| Modified scleroglucan (19) | 14,200 | 3,000 | 21.1% | 1,950 | 5.7 |
| Modified curdlan (20) | 44,000 | 18,700 | 42.5% | 2,800 | 9.0 |
| Modified curdlan (21) | 21,300 | 1,900 | 8.9% | 3,900 | 5.0 |

Example 12: Synthesis of Pachymaran in which Poly(Lactic-Co-Glycolic Acid) is Modified (Modified Pachymaran (22))

(1) Oxidative Cleavage Reaction of Pachyman (Synthesis of Pachymaran)

After 1 g of pachyman (Bio Supply) was mixed with 120 ml of water, 40 ml of 0.1 M sodium periodate solution was added, followed by stirring at room temperature for 40 hours, and then the reactant was collected by centrifugation. The reactant was mixed with 54 ml of water, 27 ml of a solution containing 216 mg of sodium borohydride was added, followed by stirring at room temperature for 28 hours, and then the reactant was collected by centrifugation. The reactant was mixed with 70 mL of 0.05 M sulfuric acid solution and the solution was stirred at room temperature for 24 hours, and then 0.91 g of pachymaran was collected.

(2) Hydrolysis Reaction of Pachymaran (Synthesis of Pachymaran Hydrolysate (13))

Hydrolysis was performed in the same manner as in the above Example 11, and using 360 mg of pachymaran, 229 mg of pachymaran hydrolysate (13) (number average molecular weight 2,100) was obtained as a powder.

(3) Trimethylsilylation (TMS) Reaction of Pachymaran (Synthesis of Trimethylsilylated Pachymaran (15))

Trimethylsilylation was performed in the same manner as in Example 11 mentioned above and, using 200 mg of pachymaran hydrolysate (13), 325 mg of trimethylsilylated pachymaran (15) was obtained as a white solid.

(4) Modification Reaction of Poly(Lactic-Co-Glycolic Acid) to Pachymaran (Synthesis of Modified Pachymaran (22))

In the same manner as in the above Example 11, 300 mg of a trimethylsilylated pachymaran (15) was reacted with tert-butoxypotassium (tBuOK) and a monomer (a mixture of (DL)-lactide and glycolide with a molar ratio of 1:1) of 35-fold mol of tBuOK to obtain 353 mg of a modified pachymaran (22) as a white solid.

Figure 19:
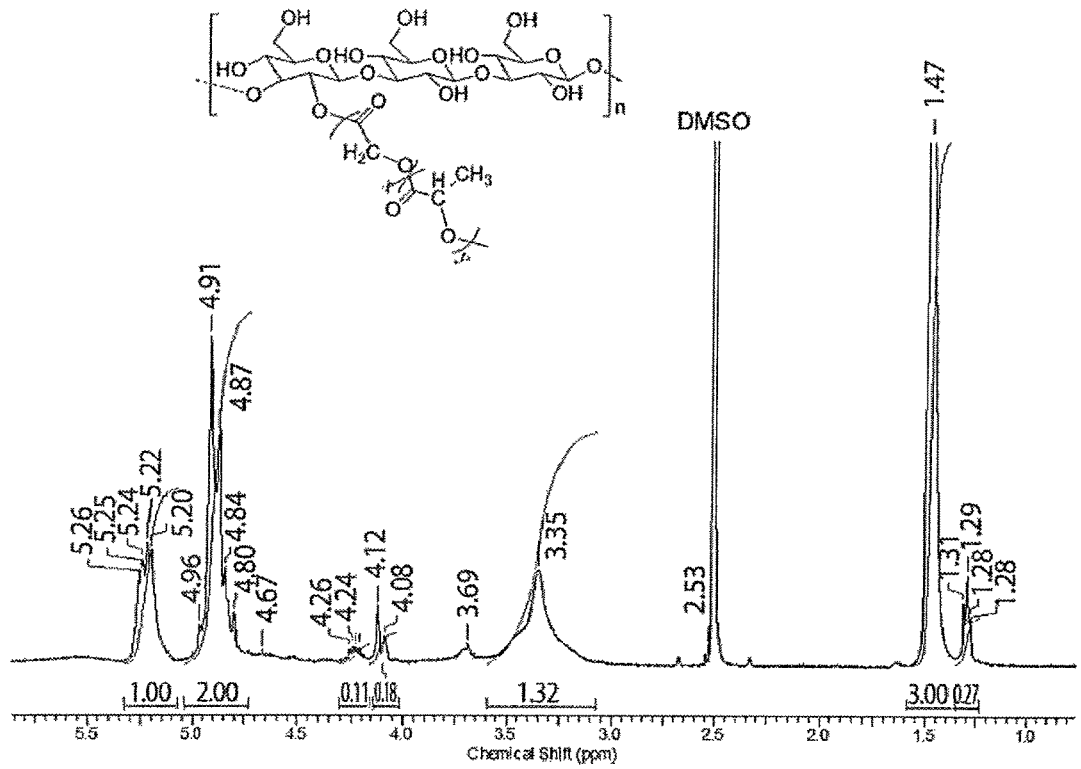
FIG. 19 shows the results of $^1$H-NMR measurement of a modified pachymaran (22).

The results of assessment of modified pachymaran (22) are shown in Table 10. Each value was determined by GPC measurement and $^1$H-NMR measurement in the same manner as in Example 11 mentioned above (FIG. 19: $^1$H-NMR measurement of modified pachymaran (22)).

TABLE 10

Results of analysis of modified pachymaran (22)

| | Molecular weight of modified pachymaran | Molecular weight of pachymaran | Proportion of pachymaran | Molecular weight of graft chain | Number of graft chains |
|---|---|---|---|---|---|
| Modified pachymaran (22) | 13,800 | 2,100 | 15.2% | 1,300 | 9.0 |

Example 13: Preparation of Particles 2 (Pachyman Particle (16), Sizofiran Particle (17), *Aureobasidium pullulans* Glucan Particle (18), Scleroglucan Particle (19), Curdlan Particle (20), Pachymaran Particle (21), Dextran Comparative Particle (22)) Prepared by the O/W Emulsion Method By dissolving 10 mg of modified pachyman (16) in 1 ml of ethyl acetate, a polymer solution was prepared. The polymer solution was added dropwise to 4 ml of a 1% (w/v) polyvinyl alcohol aqueous solution, followed by stirring at 11,000 rpm for 5 minutes using a mixer (Polytron, PT2100S) to prepare an O/W emulsion solution. Ethyl acetate was removed from the O/W emulsion solution by the solvent evaporation method, and the solution was used as a particle suspension. The suspension was transferred to a 15 ml tube, and centrifuged at 8,000 rpm for 10 minutes to precipitate the particle. After the supernatant was removed, the particle was resuspended in 10 ml of distilled water, and the particle was reprecipitated by centrifugation under the above conditions. This washing operation was repeated once again, the supernatant was removed, and then the particle was suspended in 1.8 ml of an aqueous solution containing 5% (w/v) mannitol and 0.1% (w/v) polysorbate 80. The suspension was pre-frozen with liquid nitrogen, and then freeze-dried for 12 hours at a trap cooling temperature of −45° C. and under vacuum of 20 Pa using a freeze-drying device (Tokyo Rikakikai Co., Ltd., FD-1000) to obtain a pachyman particle (16).

In the same manner, sizofiran particle (17) with modified sizofiran (17) as a base material, *Aureobasidium pullulans* glucan particle (18) with modified *Aureobasidium pullulans* glucan (18) as a base material, scleroglucan particle (19) with modified scleroglucan (19) as a base material, curdlan particle (20) with modified curdlan (20) as a base material, and pachymaran particle (21) with modified pachymaran (22) as a base material were obtained.

As Comparative Example, a dextran comparative particle (22) with modified dextran (15) as a base material was obtained in the same manner.

The results of calculation of the mean particle size of the particle by the cumulant method using a dynamic light scattering device (Otsuka Electronics Co., Ltd., ELS-Z) are shown in Table 11.

TABLE 11

Results of analysis of particles (pachyman particle (16), sizofiran particle (17), *Aureobasidium pullulans* glucan particle (18), scleroglucan particle (19), curdlan particle (20), pachymaran particle (21), dextran comparative particle (22)) prepared by the O/W emulsion method

| | Base material | Particle size |
|---|---|---|
| Pachyman particle (16) | Modified pachyman (16) | 585 nm |
| Sizofiran particle (17) | Modified sizofiran (17) | 504 nm |
| *Aureobasidium pullulans* glucan particle (18) | Modified *Aureobasidium pullulans* glucan (18) | 460 nm |
| Scleroglucan particle (19) | Modified scleroglucan (19) | 470 nm |
| Curdian particle (20) | Modified curdlan (20) | 524 nm |
| Pachymaran particle (21) | Modified pachymaran (22) | 428 nm |
| Dextran comparative particle (22) | Modified dextran (15) | 543 nm |

Example 14: Preparation of Particles (Curdlan Particles Containing OVA (23) and (24), Scleroglucan Particle Containing OVA (25)) Using the S/O/W Emulsion Method By dissolving 100 mg of modified curdlan (21) in 2.6 ml of dimethyl carbonate and 200 µl of tert-butanol, a polymer solution was prepared. To the polymer solution, 1 ml of a 0.5% (w/v) OVA (ovalbumin, Sigma-Aldrich Co. LLC.) solution was added dropwise, followed by stirring at 11,000 rpm for 1 minute using a mixer (Polytron, PT2100S) to prepare a W/O emulsion solution. The W/O emulsion solution was pre-frozen with liquid nitrogen, and then freeze-dried for 12 hours at a trap cooling temperature of −45° C. and under vacuum of 20 Pa using a freeze-drying device (Tokyo Rikakikai Co., Ltd., FD-1000). The obtained solid contents were dispersed in 10 ml of ethyl acetate to prepare an S/O suspension solution. The S/0 suspension solution was added dropwise to 40 ml of 1% (w/v) polyvinyl alcohol aqueous solution, followed by stirring at 6,000 rpm for 5 minutes using a mixer (Silverson Nippon Ltd, L5M-A) to prepare an S/O/W emulsion solution. Ethyl acetate was removed from the S/O/W emulsion solution by the solvent evaporation method, and the solution was used as a particle suspension. The suspension was transferred to a 50 ml tube, and centrifuged at 8,000 rpm for 10 minutes to precipitate the particle. After the supernatant was removed, the particle was resuspended in 50 ml of distilled water, and the particle was reprecipitated by centrifugation under the above conditions. This washing operation was repeated once again, the supernatant was removed, and then the particle was suspended in 8 ml of an aqueous solution containing 5% (w/v) mannitol and 0.1% (w/v) polysorbate 80. The suspension was pre-frozen with liquid nitrogen, and then freeze-dried for 12 hours at a trap cooling temperature of −45° C. and under vacuum of 20 Pa using a freeze-drying device to obtain a curdlan particle containing OVA (23).

In the same manner, using a modified curdlan (20), a curdlan particle containing OVA (24) was obtained and, using a modified scleroglucan (19), a scleroglucan particle containing OVA (25) was obtained.

The results of assessment of particles are shown in Table 12. The mean particle size of particles was calculated by the cumulant method using a dynamic light scattering device (Otsuka Electronics Co., Ltd., ELS-Z). The encapsulation rate (w/w) of an antigen was determined by extracting the antigen from the particle using an organic solvent, by performing gel electrophoresis for the extracted antigen using a gel electrophoresis device (TEFCO), and then by staining the antigen using a colloid CBB staining kit (TEFCO).

TABLE 12

Results of analysis of particles (curdlan particles containing OVA (23) and (24), scleroglucan particle containing OVA (25)) prepared by the S/O/W emulsion method

| | Base material | Particle size | Encapsulation rate of antigen |
|---|---|---|---|
| Curdlan particle containing OVA (23) | Modified curdlan (21) | 486.9 nm | 4.97% |
| Curdlan particle containing OVA (24) | Modified curdlan (20) | 563.2 nm | 4.41% |
| Scleroglucan particle containing OVA (25) | Modified scleroglucan (19) | 441.9 nm | 4.41% |

Example 15: In Vitro Stimulation Test 2 of Modified β-Glucans (Modified Pachyman (16), Modified Sizofiran (17), Modified *Aureobasidium pullulans* Glucan (18), Modified Pachymaran (22)) in Murine Bone Marrow-Derived Dendritic Cells (BMDC)

<Methods>

After 10 mg of a modified β-glucans obtained in Example 11 (modified pachyman (16), modified sizofiran (17), modified *Aureobasidium pullulans* glucan (18), modified pachymaran (22)) were weighed, they were dissolved in 1 ml of acetonitrile to obtain a polymer solution. By dropping of the polymer solution (corresponding to 1 mg of polymer) (100 µl) into a 12-well plate and drying the plate, a polymer coated plate was obtained. On the polymer coated plate, the dendritic cells obtained in Reference Example 1 were seeded together with a culture medium so that the number of cells was $3 \times 10^5$ per well. The seeded plate was incubated for 2 days in a $CO_2$ incubator, and then the cells were strongly suspended using a micropipette to collect only cells not adhered on the plate. The collected cells were centrifuged at 1,500 rpm for 5 minutes to precipitate the cells, the supernatant was removed, and the cells were suspended in 100 µl of an RPMI medium. To the cell suspension, FITC-labeled anti-CD86 antibodies and PE-labeled anti-CD11c antibodies were added, and the suspension was allowed to stand at 4° C. for 15 minutes to perform antibody labeling reaction. After completion of the antibody labeling reaction, the expression level of an activation marker (CD86) in the dendritic cells (CD11c-positive cells) was assessed based on mean fluorescence intensity (MFI) by flow cytometry.

As Comparative Example, using a plate on which modified dextran (15) obtained in Comparative Example 1 was coated in the same manner, the expression level of the activation marker was compared in the same manner. As another Comparative Example, 1 mg of unmodified β-glucans (pachyman hydrolysate (7), sizofiran hydrolysate (8), Aureobasidium pullulans glucan hydrolysate (9), pachymaran hydrolysate (13)) obtained in Example 11 or 100 μg of poly I:C (Sigma-Aldrich Co. LLC.) with known immunopotentiating capacity were/was added to a culture medium, and the expression level of the activation marker was compared in the same manner.

<Results>

Figure 20:
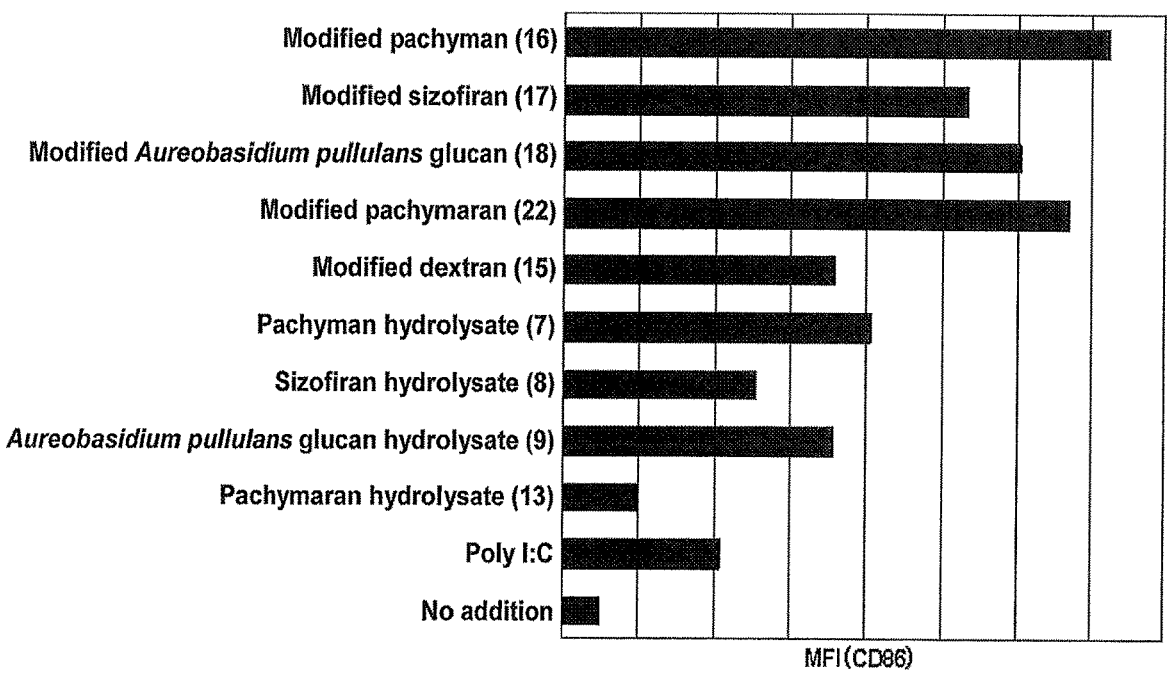
FIG. 20 shows the results of in vitro stimulation test 2 of a modified β-glucan.

Mean fluorescence intensity (MFI), an index of the expression level of CD86, an activation marker of dendritic cells, is shown in FIG. 20. When a modified β-glucan was used, the expression level of CD86 was higher than that when modified dextran (15) was used, revealing that modified β-glucan has potent dendritic cell activation capacity. When an unmodified β-glucan was used, the expression level of CD86 was lower than that when modified β-glucan was used, revealing that modification of poly(hydroxy acid) to β-glucan is important for immunopotentiating capacity. Not only linear modified β-glucans (Example 4, modified curdlans (9) to (12); present Example, modified pachyman (16)) but also branched modified β-glucans (present Example: modified sizofiran (17), modified Aureobasidium pullulans glucan (18)) and derivatized modified β-glucan (present Example: modified pachymaran (22)) were found to have immunopotentiating capacity.

Example 16: In Vitro Stimulation Test 2 of Particles with Modified β-Glucan as a Base Material (Pachyman Particle (16), Sizofiran Particle (17), Aureobasidium pullulans Glucan Particle (18), Scleroglucan Particle (19), Curdlan Particle (20), Pachymaran Particle (21)) in Murine Bone Marrow-Derived Dendritic Cells (BMDC)

The dendritic cells obtained in Reference Example 1 were seeded together with a culture medium on a 12-well plate so that the number of cells was $3\times10^5$ per well, and 0.05 mg of particles with modified β-glucan as a base material (pachyman particle (16), sizofiran particle (17), Aureobasidium pullulans glucan particle (18), scleroglucan particle (19), curdlan particle (20), pachymaran particle (21)) were further added. The seeded plate was incubated for 2 days in a $CO_2$ incubator, and then the cells were strongly suspended using a micropipette to collect only cells not adhered on the plate. The collected cells were centrifuged at 1,500 rpm for 5 minutes to precipitate the cells, the supernatant was removed, and the cells were suspended in 100 μl of an RPMI medium. To the cell suspension, FITC-labeled anti-CD86 antibodies and PE-labeled anti-CD11c antibodies were added, and the suspension was allowed to stand at 4° C. for 15 minutes to perform antibody labeling reaction. After completion of the antibody labeling reaction, the expression level of an activation marker (CD86) in the dendritic cells (CD11c-positive cells) was assessed based on mean fluorescence intensity (MFI) by flow cytometry.

As Comparative Example, 0.05 mg of a particle with dextran as a base material (dextran comparative particle (22)) was added to a culture medium, and the expression level of the activation marker was compared in the same manner.

<Results>

Figure 21:
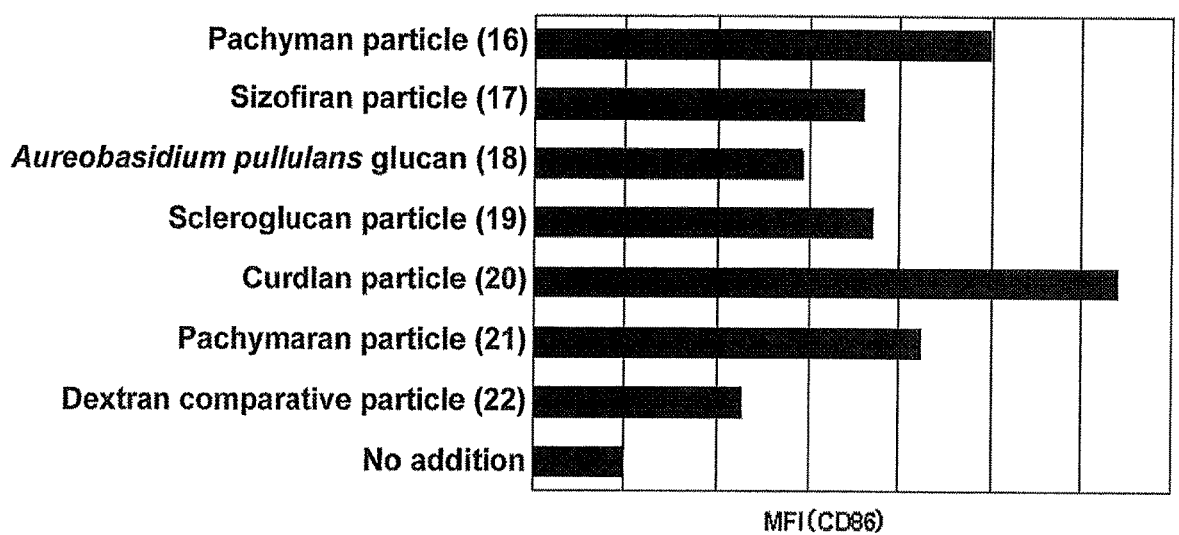
FIG. 21 shows the results of in vitro stimulation test 3 of particles with a modified β-glucan as a base material.

Mean fluorescence intensity (MFI), an index of the expression level of CD86 in each particle, is shown in FIG. 21. When particles with a modified β-glucan as a base material (pachyman particle (16), sizofiran particle (17), Aureobasidium pullulans glucan particle (18), scleroglucan particle (19), curdlan particle (20), pachymaran particle (21)) were used, the expression level of CD86 was higher than that when no particles were added and when particle with modified dextran as a base material (dextran comparative particle (22)) was used, revealing that particles with modified fβ-glucan as a base material strongly activate dendritic cells.

Example 17: In Vivo Test 4 of Modified β-Glucan in Mice (Assessment by IFN-γ Production Capacity)

<Methods>

Mice used for the experiment were 5-week male C57BL/6NCR mice purchased from Japan SLC, Inc. The mice were raised under free-feeding conditions with a 12-hour day/night cycle at an in-house rearing facility for 1 week and acclimated to the environment.

Administration was performed to the mice under the conditions shown in Table 13. Under conditions (17) to (19), the particles prepared in Example 14 (curdlan particles containing OVA (23) and (24), a scleroglucan particle containing OVA (25)) were dispersed in 50 μl of 4% (w/v) mannitol aqueous solution, and the solution was administered to foot pads on both hind legs with a 29G injection needle (Terumo Myjector). Under comparative condition (20), OVA (Sigma-Aldrich Co. LLC.) and a curdlan hydrolysate (12) were administered in the same manner.

Under all conditions, the second administration was performed 3 days after the first administration in the same manner, the third administration was performed 7 days after the first administration in the same manner, and the fourth administration was performed 10 days after the first administration in the same manner.

The mice after administration were raised under free-feeding conditions and an environment where water supply is possible, and euthanized with carbonic acid gas 16 days after the first administration. Lymph nodes below the knee near the administration site were aseptically removed, the contained cells were dispersed, and then filtered with a 200 μm filter (AS ONE Corporation, FILCONS, 120-22S) to remove debris. The collected cells were suspended in an RPMI1640 medium (hereinafter referred to as RPMI medium) containing 10% FBS (Sigma-Aldrich Co. LLC.), 100 IU/ml penicillin (Life Technologies, Inc.), and 100 IU/ml streptomycin (Life Technologies, Inc.), seeded on a 96-well plate (IWAKI & Co., Ltd., Flat Bottom Tissue Culture Polystyrene) so that the number of cells was $5\times10^5$ per well, and an RPMI medium containing 10 μg of OVA and 0.75 μg of 2-mercaptoethanol was further added to stimulate the cells. The seeded plate was incubated in a $CO_2$ incubator for 48 hours, the culture supernatant was collected, and the concentration of IFN-γ produced from each cell group was measured by the ELISA method (Mabtech AB, Mouse IFN-gamma ELISA kit [HRP]).

<Results>

Figure 22:
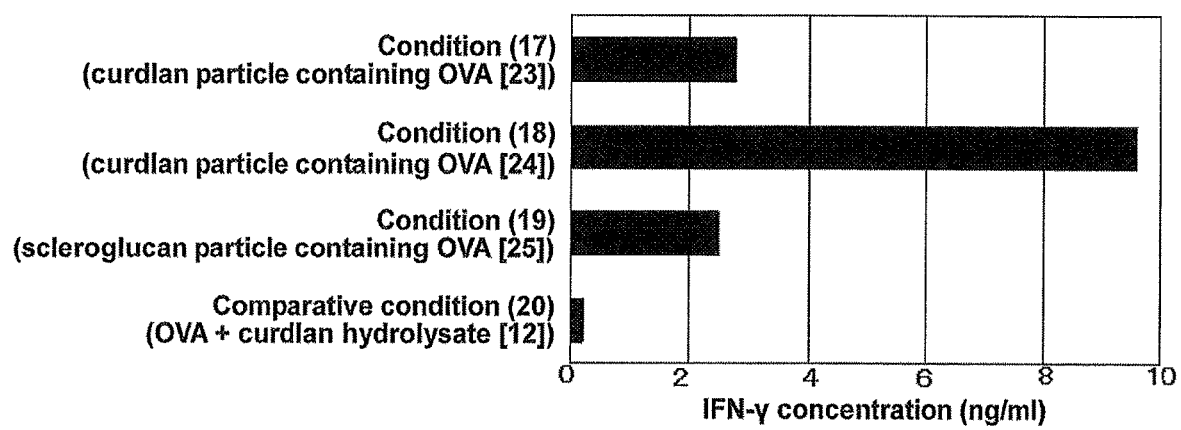
FIG. 22 shows the results of in vivo test 4 of a modified β-glucan.

The amount of IFN-γ produced by lymph node cells is shown in FIG. 22. IFN-γ is an index of activation of cell-mediated immunity. Under the condition in which a particle containing OVA with modified curdlan as a base material was administered (condition (17)), stronger production of IFN-γ was found than under the condition in which OVA and unmodified curdlan were administered (comparative condition (20)), revealing that modified β-glucan has more potent immunopotentiating capacity than β-glucan also in vivo. Under the condition in which a particle containing OVA with high molecular weight modified curdlan as a base material was administered (condition (18)) and the condition in which a particle containing OVA with branched modified scleroglucan as a base material was administered (condition (19)), stronger production of IFN-γ was also found, showing that modified β-glucan has potent immunopotentiating capacity regardless of molecular weight and whether it is linear or branched.

TABLE 13

Administration conditions in vivo test 4 of modified β-glucan in mice

| | Substance administered | Frequency of administration |
|---|---|---|
| Condition (17) | 0.5 mg of curdlan particle containing OVA (23) | 4 |
| Condition (18) | 0.5 mg of curdlan particle containing OVA (24) | 4 |
| Condition (19) | 0.5 mg of scleroglucan particle containing OVA (25) | 4 |
| Comparative condition (20) | 25 μg of OVA, 0.5 mg of curdlan hydrolysate (12) | 4 |

INDUSTRIAL APPLICABILITY

An immunopotentiator of the present invention can be utilized as a medicine, particularly as an immunopotentiator for a vaccine for the treatment and/or prevention of infection, cancer, and the like.

The invention claimed is:

1. A method for immunopotentiation, comprising administering in vivo an immunopotentiator as an active ingredient to an organism or a subject,
  wherein the immunopotentiator comprises, as an active ingredient, a modified β-glucan in which β-glucan having immunopotentiating effect and poly(hydroxy acid) are covalently bonded, and
  wherein β-glucan is a polymer of glucose linked by at least one β-1,3 bond and/or at least one β-1,6 bond.

2. The method according to claim 1, wherein modified β-glucan is a graft type polymer composed of the main chain of β-glucan and the side chain of poly(hydroxy acid).

3. The method according to claim 1, wherein β-glucan is curdlan, pachyman, laminaran, lichenan, sizofiran, lentinan, scleroglucan, *Aureobasidium pullulans* glucan, or pachymaran.

4. The method according to claim 1, wherein poly(hydroxy acid) is a poly(lactic-co-glycolic acid), polylactic acid, or polyglycolic acid.

5. The method according to claim 1, wherein the immunopotentiator comprises a particle of the modified β-glucan as an active ingredient.

6. The method according to claim 1, further comprising administering in vivo an antigen as an active ingredient to the organism or the subject.

7. A method for immunopotentiation, comprising administering in vivo an immunopotentiator as an active ingredient to an organism or a subject,
  wherein the immunopotentiator comprises, as an active ingredient, a modified β-glucan in which β-glucan and poly(hydroxy acid) are covalently bonded, and
  wherein β-glucan is a polymer of glucose linked by at least one β-1,3 bond and/or at least one β-1,6 bond,
  wherein β-glucan is curdlan, pachyman, laminaran, lichenan, sizofiran, lentinan, scleroglucan, *Aureobasidium pullulans* glucan, or pachymaran.

8. A method of treatment of cancer, comprising administering in vivo an immunopotentiator and a cancer antigen as active ingredients to an organism or a subject,
  wherein the immunopotentiator comprises, as an active ingredient, a modified β-glucan in which β-glucan having immunopotentiating effect and poly(hydroxy acid) are covalently bonded, and
  wherein β-glucan is a polymer of glucose linked by at least one β-1,3 bond and/or at least one β-1,6 bond.

9. The method according to claim 8, wherein β-glucan is curdlan, pachyman, laminaran, lichenan, sizofiran, lentinan, scleroglucan, *Aureobasidium pullulans* glucan, or pachymaran.

10. A composition comprising an antigen,
  and a modified β-glucan in which β-glucan and poly(hydrox acid) are covalently bonded, and
  wherein β-glucan is a polymer of glucose linked by at least one β-1,3 bond and/or at least one β-1,6 bond, wherein
  β-glucan is curdlan, pachyman, laminaran, lichenan, sizofiran, lentinan, scleroglucan, *Aureobasidium pullulans* glucan, or pachymaran.

* * * * *